US012680949B2

(12) United States Patent 
Uchiyama et al.

(10) Patent No.: US 12,680,949 B2 
(45) Date of Patent: Jul. 14, 2026

(54) METHOD FOR CHARACTERIZING MOLECULE DELIVERY PARTICLES

(71) Applicant: OSAKA UNIVERSITY, Osaka (JP)

(72) Inventors: Susumu Uchiyama, Osaka (JP); Takahiro Maruno, Osaka (JP); Tetsuo Torisu, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 273 days.

(21) Appl. No.: 18/287,336

(22) PCT Filed: Mar. 24, 2022

(86) PCT No.: PCT/JP2022/014106 
§ 371 (c)(1), 
(2) Date: Oct. 18, 2023

(87) PCT Pub. No.: WO2022/224697 
PCT Pub. Date: Oct. 27, 2022

(65) Prior Publication Data 
US 2024/0060878 A1 Feb. 22, 2024

(30) Foreign Application Priority Data

Apr. 19, 2021 (JP) ................................. 2021-070724

(51) Int. Cl. 
*G01N 21/33* (2006.01) 
*G16B 40/10* (2019.01)

(52) U.S. Cl. 
CPC ............. *G01N 21/33* (2013.01); *G16B 40/10* (2019.02)

(58) Field of Classification Search 
CPC .. G01N 21/33; G01N 15/01; G01N 2015/045; G01N 15/042; G16B 40/10; 
(Continued)

(56) References Cited

U.S. PATENT DOCUMENTS

| | | |
|---|---|---|
| 2009/0312482 A1 | 12/2009 | Feldermann et al. |
| 2012/0302694 A1 | 11/2012 | Feldermann et al. |

(Continued)

FOREIGN PATENT DOCUMENTS

| | | |
|---|---|---|
| JP | 3-106931 | 5/1991 |
| JP | 2000-344791 | 12/2000 |

(Continued)

OTHER PUBLICATIONS

Brown, Patrick et al., "Density Contrast Sedimentation Velocity for the Determination of Protein Partial-Specific Volumes", PLoS One, 2011, vol. 6, Issue 10, pp. 1-16. 
(Continued)

*Primary Examiner* — Uzma Alam 
*Assistant Examiner* — Gisselle M Gutierrez 
(74) *Attorney, Agent, or Firm* — Wenderoth, Lind & Ponack, L.L.P.

(57) ABSTRACT

An objection is to provide a method for characterizing a molecule delivery particle, the method comprising determining a molar concentration thereof.

The method for characterizing a molecule delivery particle, the method comprising subjecting a molecule delivery particle comprising a first particle and a second particle to particle separation with optical measurement to determine an increment in refractive index of each of the first particle and the second particle; and determining a molar concentration of each of the first particle and the second particle based on the increment in refractive index, a molecular weight, and a specific refractive index increment of each of the first particle and the second particle.

10 Claims, 12 Drawing Sheets

(58) Field of Classification Search
CPC ...... A61K 48/0091; C12N 2750/14143; C12N
2750/14151; C12N 15/86
See application file for complete search history.

(56) References Cited

U.S. PATENT DOCUMENTS

| | | | |
|---|---|---|---|
| 2016/0011099 A1* | 1/2016 | Shih ....................... G01N 33/94 |
| | | | 356/413 |
| 2016/0216249 A1* | 7/2016 | Sass ..................... G01N 21/274 |
| 2018/0180525 A1 | 6/2018 | O'Riordan et al. | |
| 2020/0225139 A1 | 7/2020 | O'Riordan et al. | |
| 2021/0082541 A1 | 3/2021 | Chen et al. | |
| 2021/0389306 A1 | 12/2021 | Ota et al. | |
| 2022/0308022 A1* | 9/2022 | Bhat ....................... C12N 15/86 |

FOREIGN PATENT DOCUMENTS

| | | |
|---|---|---|
| JP | 2002-86155 | 3/2002 |
| JP | 4686714 | 2/2011 |
| JP | 2011-524449 | 9/2011 |
| JP | 2018-505695 | 3/2018 |
| JP | 2020-161475 | 10/2020 |
| JP | 7454883 B2 * | 3/2024 ........ A61K 48/0091 |
| WO | 2016/118520 | 7/2016 |
| WO | 2020/067396 | 4/2020 |
| WO | 2021/062164 | 4/2021 |

OTHER PUBLICATIONS

English translation of the Written Opinion of the International Searching Authority issued Jun. 14, 2022 in International (PCT) Application No. PCT/JP2022/014106.

International Search Report issued Jun. 14, 2022 in International (PCT) Application No. PCT/JP2022/014106.

Extended European Search Report issued Jan. 15, 2025 in corresponding European Patent Application No. 22791473.6.

* cited by examiner

| Parameter | | AAV5-EP | AAV5-FP |
|---|---|---|---|
| $s_{20,w}$ | | 67.3 | 93.7 |
| v-bar PBS (cm$^3$ g$^{-1}$) | | 0.723 | 0.688 |
| v-bar Global Fit (cm$^3$ g$^{-1}$) | | 0.722 | 0.686 |
| f/f$_0$ Global Fit | | 1.327 | 1.318 |
| Molecular weight (k Da) | | 3695.9 (3705.5) | 4914.2 (4507.0) |
| $D \times 10^7$ (cm$^2$ sec$^{-1}$) | SEDFIT | 1.56 | 1.58 |
| | HYDROPRO | 1.57 | 1.57 |

The values in parentheses are calculated values determined by the chemical composition.

230 nm 260 nm 280 nm

Refractive index

Fig. 3A                     Fig. 3B 230 nm 260 nm 280 nm

Fig. 9A
| | $n_{copies}$ | | | | | | | | | | | |
|---|---|---|---|---|---|---|---|---|---|---|---|---|
| | 1 | | | | 2 | | | | 3 | | | |
| | Mw (kDa) | v-bar (cm³g⁻¹) | s (S) | $N_{nucleotide}$ | Mw (kDa) | v-bar (cm³g⁻¹) | s (S) | $N_{nucleotide}$ | Mw (kDa) | v-bar (cm³g⁻¹) | s (S) | $N_{nucleotide}$ |
| 0 | 3695.9 | 0.722 | 65.3 | 0 | 7391.8 | 0.722 | 95.1 | 0 | 11087.7 | 0.722 | 122.9 | 0 |
| 0.5 | 4096.7 | 0.702 | 75.7 | 1300 | 7792.6 | 0.712 | 102.7 | 650 | 11488.5 | 0.715 | 128.6 | 433 |
| 1 | 4497.4 | 0.686 | 85.7 | 2599 | 8193.3 | 0.702 | 110.2 | 1300 | 11889.2 | 0.708 | 135.1 | 866 |
| 1.5 | 4898.2 | 0.672 | 95.4 | 3899 | 8594.1 | 0.694 | 117.5 | 1949 | 12290.0 | 0.702 | 141.4 | 1300 |
| 2 | 5298.9 | 0.661 | 104.7 | 5198 | 8994.8 | 0.686 | 124.7 | 2599 | 12690.7 | 0.696 | 147.7 | 1733 |
| 2.5 | 5699.7 | 0.651 | 113.7 | 6498 | 9395.6 | 0.679 | 131.8 | 3249 | 13091.5 | 0.691 | 154.0 | 2166 |
| 3 | 6100.4 | 0.642 | 122.5 | 7797 | 9796.3 | 0.672 | 138.8 | 3899 | 13492.2 | 0.686 | 160.1 | 2599 |
The values were calculated using the molecular weight of AAV5-EP, partial-specific volume of AAV5-EP and AAV5-FP, and $R_0$ AAV5-FP determined by AUC experiments in addition to the molecular weight and partial-specific volume of ssDNA.
Fig. 9B
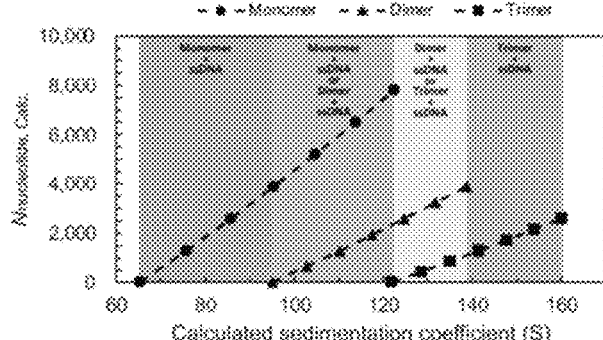
Fig. 9C
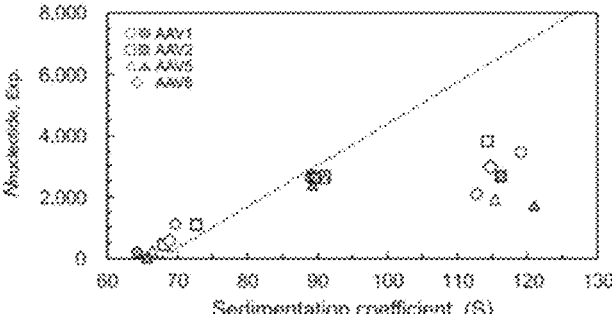

Fig. 12

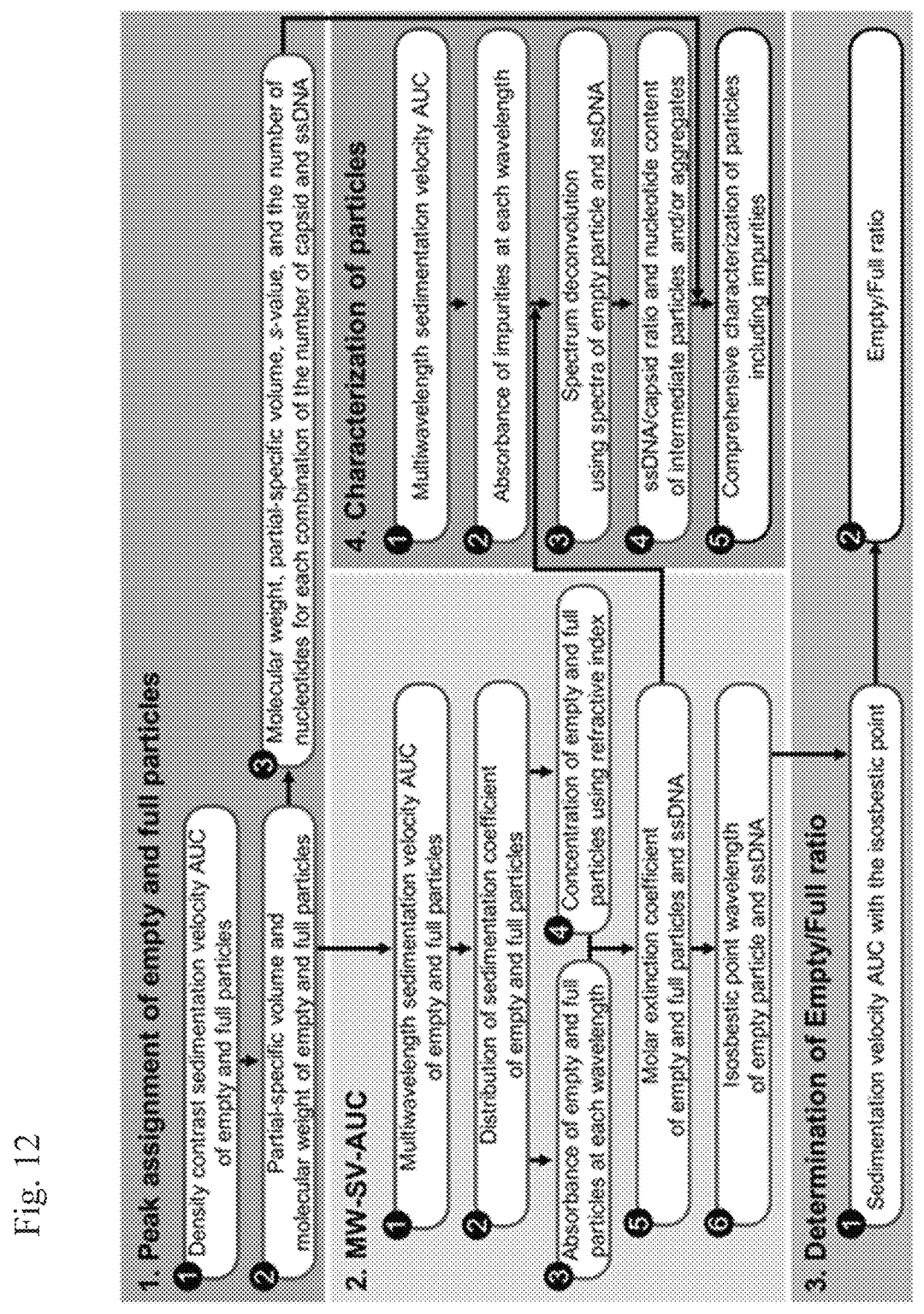

1. Peak assignment of empty and full particles

① Density contrast sedimentation velocity AUC of empty and full particles

② Partial-specific volume and molecular weight of empty and full particles

③ Molecular weight, partial-specific volume, s-value, and the number of nucleotides for each combination of the number of capsid and ssDNA

2. MW-SV-AUC

① Multiwavelength sedimentation velocity AUC of empty and full particles

② Distribution of sedimentation coefficient of empty and full particles

③ Absorbance of empty and full particles at each wavelength

④ Concentration of empty and full particles using refractive index

⑤ Molar extinction coefficient of empty and full particles and ssDNA

⑥ Isosbestic point wavelength of empty particle and ssDNA

3. Determination of Empty/Full ratio

① Sedimentation velocity AUC with the isosbestic point

② Empty/Full ratio

4. Characterization of particles

① Multiwavelength sedimentation velocity AUC

② Absorbance of impurities at each wavelength

③ Spectrum deconvolution using spectra of empty particle and ssDNA

④ ssDNA/capsid ratio and nucleotide content of intermediate particles and/or aggregates ⑤ Comprehensive characterization of particles including impurities

METHOD FOR CHARACTERIZING MOLECULE DELIVERY PARTICLES

TECHNICAL FIELD

The present invention provides a method for characterizing a molecule delivery particle. The invention also provides a program that executes the method for characterizing a molecule delivery particle.

BACKGROUND ART

Particles for delivering various molecules, such as a therapeutic compound, a gene, and a nutrient, are used in various technical fields including a drug delivery system. A drug delivery system (DDS) is a technology aimed at efficiently delivering a drug to a target site. Examples of a drug carrier used in a DDS include a liposome, which is a lipid capsule composed of a phospholipid bilayer, a micelle composed of polyethylene glycol (PEG) and polylactic acid (PLA), and a particle composed of a polylactic acid-glycolic acid copolymer (also referred to as PLGA). In the field of gene therapy, a virus vector is used as a gene carrier.

A recombinant adeno-associated virus (AAV) vector has become a promising platform for gene therapy. In a step of producing an AAV vector including a single-stranded DNA (ssDNA) genome of about 4.7 kb, it is difficult to avoid contamination with a virus particle not including ssDNA (empty particle) and a virus particle including incomplete ssDNA (intermediate particle).

Anion exchange chromatography or analytical ultracentrifugation (AUC) is used to characterize an AAV vector, particularly for evaluating the ratio of an empty particle to a particle including a complete ssDNA genome (full particle). In chromatographic analysis, evaluation can be carried out in a small amount ($10^{10}$ vg$^2$ or less) in a short time, but for good separation and quantification of an empty particle and a full particle, optimization of analytical conditions including a column, a mobile phase, and an elution condition is required and is cumbersome. An empty and full particle can be directly observed and counted with an electron microscope at high magnification. However it is possible to evaluate a particle within a field of view, but it is practically challenging to evaluate an overall picture of the system.

Sedimentation velocity analytical ultracentrifugation (SV-AUC) is a powerful technique for characterizing the size distribution of a high molecular weight molecule in a solution. A recent advance in AUC analysis, particularly a computational method, has made it possible to model the sedimentation process of a nonuniform mixture and quantify the distribution of a sedimentation coefficient in a solution. AUC analysis is carried out without a chemical modification such as interaction with the column or negative staining. In addition, it is possible to recover most of the sample after the measurement. A method for characterizing a recombinant virus particle using sedimentation velocity analytical ultracentrifugation is known (Patent Literature 1).

CITATION LIST

Patent Literature 1: JP 2018-505695 A

SUMMARY

Technical Problem

Including an empty particle and an intermediate particle in an AAV vector-based formulation can reduce the overall therapeutic effect of the formulation and cause an undesirable immune response. The AAV vector-based formulation can also include a further component such as an AAV vector aggregate. An accurate and reliable method is necessary to analyze a particle-related impurity in an AAV vector. However, the characterization of a recombinant virus particle by a conventional method has been insufficient. An object of the present disclosure is to provide a novel method that enables the characterization of a recombinant virus particle that cannot be achieved by a conventional method by using sedimentation velocity analytical ultracentrifugation.

An object of the present disclosure is to provide a novel method for characterizing a molecule delivery particle, including determining molecular weight. An object of the present disclosure is to provide a novel method for characterizing a molecule delivery particle, including determining a molar concentration. An object of the present disclosure is to provide a novel method for characterizing a molecule delivery particle, including determining a molar extinction coefficient.

An object of the present disclosure is to provide a novel method for characterizing a molecule delivery particle, including determining a quantitative ratio. An object of the present disclosure is to provide a novel method for characterizing a molecule delivery particle, including determining a quantitative ratio based on measurement at an isosbestic point without using a molar extinction coefficient.

An object of the present disclosure is to provide a novel method for characterizing a molecule delivery particle, including determining a degree of contribution of a third particle to an absorbance. An object of the present disclosure is to provide a novel method for characterizing a molecule delivery particle, including determining quality.

An object of the present disclosure is to provide a novel program that executes the method for characterizing a molecule delivery particle described above.

Solution to Problem

The present disclosure provides the following method for characterizing a molecule delivery particle, a program for executing the method, a method for determining a molar extinction coefficient of a first particle, and a method for determining a molar extinction coefficient of a polynucleotide of a predetermined chain length:

Item 1

A method for characterizing a molecule delivery particle, the method comprising:

subjecting a molecule delivery particle comprising a first particle and a second particle to particle separation with optical measurement to determine an increment in refractive index of each of the first particle and the second particle; and determining a molar concentration of each of the first particle and the second particle based on the increment in refractive index, a molecular weight, and a specific refractive index increment of each of the first particle and the second particle.

Item 2

The method according to item 1, wherein the method comprises:

subjecting the molecule delivery particle to particle separation with optical measurement at a plurality of measurement wavelengths to determine an absorbance of each of the first particle and the second particle for each measurement wavelength of the plurality of measurement wavelengths; and determining a molar extinction coefficient of each of the first particle and the second particle for the each measurement wavelength based on the absorbance of each of the first particle and the second particle and the molar concentration of each of the first particle and the second particle.

Item 3

The method according to item 2, wherein the first particle comprises a first coat and a first delivery molecule, and the second particle comprises a second coat; and the method comprises:

determining a molar extinction coefficient of the first particle and the second particle for the each measurement wavelength based on the absorbance of each of the first particle and the second particle and the molar concentration of each of the first particle and the second particle; and determining a molar extinction coefficient of the first delivery molecule for the each measurement wavelength by subtracting the molar extinction coefficient of the second particle from the molar extinction coefficient of the first particle.

Item 4

The method according to item 3, wherein the method comprises:

identifying an isosbestic point at which the molar extinction coefficient of the second particle and the molar extinction coefficient of the first delivery molecule are consistent with each other; and determining a quantitative ratio between the first particle and the second particle by using the absorbance of each of the first particle and the second particle at the isosbestic point.

Item 5

A method for characterizing a molecule delivery particle, the method comprising:

subjecting a molecule delivery particle comprising a first particle and a second particle to particle separation with optical measurement at a measurement wavelength for which a molar extinction coefficient of each of the first particle and the second particle is determined, to determine an absorbance of each of the first particle and the second particle; and determining a quantitative ratio between the first particle and the second particle by using the absorbance of each of the first particle and the second particle and the determined molar extinction coefficient of each of the first particle and the second particle.

Item 6

A method for characterizing a molecule delivery particle, the method comprising:

subjecting a molecule delivery particle comprising a first particle and a second particle to particle separation with optical measurement at an isosbestic point to determine an absorbance of each of the first particle and the second particle; and determining a quantitative ratio between the first particle and the second particle by using the absorbance of each of the first particle and the second particle.

Item 7

The method according to any one of items 3 to 5, wherein the molecule delivery particle further comprises a third particle, and the third particle comprises a third coat and optionally comprises a third delivery molecule; and the method comprises:

determining an absorbance of the third particle for the each measurement wavelength by particle separation with optical measurement of the molecule delivery particle; and determining a degree of contribution of the molar extinction coefficient of the second particle and the molar extinction coefficient of the first delivery molecule to the absorbance of the third particle.

Item 8

The method according to item 7, wherein the method further comprises: determining a proportion of the third particle; and/or determining a concentration of each of the third coat and the third delivery molecule, based on the degree of contribution.

Item 9

The method according to any one of items 4 to 6, wherein the method comprises determining that the molecule delivery particle has a predetermined quality when the quantitative ratio exceeds a first threshold, or the method according to item 8, wherein the method comprises determining a quantitative ratio of the first particle or the second particle to the molecule delivery particle based on the molar concentration of the first particle, the molar concentration of the second particle, the concentration of the third coat, and the concentration of the third delivery molecule, and determining that the molecule delivery particle has a predetermined quality when the quantitative ratio exceeds a first threshold.

Item 10

A method for characterizing a molecule delivery particle, the method comprising:

subjecting a molecule delivery particle to particle separation with optical measurement at a first measurement wavelength and a second measurement wavelength to determine an absorbance of the molecule delivery particle for each of the first measurement wavelength and the second measurement wavelength; and determining an absorbance ratio from the absorbance of the molecule delivery particle at the first measurement wavelength and the absorbance of the molecule delivery particle at the second measurement wavelength.

5

Item 11

The method according to any one of items 1 to 10, wherein the particle separation is centrifugation, chromatography, or field flow fractionation.

Item 12

A method for characterizing a molecule delivery particle, the method comprising:
  subjecting a first solution comprising the molecule delivery particle and a solvent to centrifugation with optical measurement to determine a sedimentation coefficient of the molecule delivery particle in the first solution;
  subjecting a second solution comprising the molecule delivery particle and an isotopically labeled solvent to centrifugation with optical measurement to determine a sedimentation coefficient of the molecule delivery particle in the second solution;
  determining a partial specific volume of the molecule delivery particle based on the sedimentation coefficient of the molecule delivery particle in the first solution and the sedimentation coefficient of the molecule delivery particle in the second solution; and
  determining a molecular weight of the molecule delivery particle based on the sedimentation coefficient of the molecule delivery particle in the first solution, the sedimentation coefficient of the molecule delivery particle in the second solution, and the partial specific volume of the molecule delivery particle.

Item 13

The method according to any one of items 1 to 12, wherein the molecule delivery particle is a virus particle, a liposome, an albumin particle, a micelle, or a polylactic acid-glycolic acid copolymer particle.

Item 14

The method according to item 13, wherein the virus particle is an adeno-associated virus, an adenovirus, a herpes virus, a Sendai virus, a stealth virus, a lentivirus, or a retrovirus.

Item 15

A program that, when loaded into a control unit of a computer, causes the computer to execute the method according to any one of items 1 to 14.

Item 16

A method for determining a molar extinction coefficient of a first particle, wherein
  the first particle comprises a first coat and a first polynucleotide of a first chain length, the method comprising:
  dividing a molar extinction coefficient of a second polynucleotide of a predetermined chain length by a value of the predetermined chain length to calculate an average molar extinction coefficient per nucleotide,
  multiplying the average molar extinction coefficient per nucleotide by a value of the first chain length to calculate a molar extinction coefficient of the first polynucleotide; and

combining a molar extinction coefficient of the first coat and the molar extinction coefficient of the first polynucleotide to determine a molar extinction coefficient of the first particle.

Item 17

A method for determining a molar extinction coefficient of a polynucleotide of a predetermined chain length, the method comprising:
  when measuring a molecule delivery particle comprising the polynucleotide at a predetermined measurement wavelength, multiplying an average molar extinction coefficient per nucleotide at any one wavelength listed in the following table that is the same as or corresponds to the predetermined measurement wavelength by a value of the predetermined chain length to determine a molar extinction coefficient of the polynucleotide at the any one wavelength.

TABLE

| Wavelength (nm) | Average molar extinction coefficient per nucleotide [$\times 10^7$ L mol$^{-1}$ cm$^{-1}$] |
|---|---|
| 230 | $4.391 \times 10^{-4}$ |
| 235 | $4.849 \times 10^{-4}$ |
| 240 | $5.463 \times 10^{-4}$ |
| 245 | $6.339 \times 10^{-4}$ |
| 250 | $7.488 \times 10^{-4}$ |
| 255 | $8.336 \times 10^{-4}$ |
| 260 | $8.648 \times 10^{-4}$ |
| 265 | $8.058 \times 10^{-4}$ |
| 270 | $7.256 \times 10^{-4}$ |
| 275 | $6.255 \times 10^{-4}$ |
| 280 | $5.060 \times 10^{-4}$ |

BRIEF DESCRIPTION OF DRAWINGS

FIG. 1A is superimposed diagrams of sedimentation coefficient distributions of AAV5-EP (left) and AAV5-FP (right) in density contrast SV-AUC experiments. The black, red, and blue lines represented the distributions at 0%, 32.5%, and 65% of a buffer solution including $H_2^{18}O$. The distributions were normalized using the experimentally determined partial specific volume of each component and the calculated density and viscosity. FIG. 1B (left) is a table showing hydrodynamic parameters and calculated molecular weights obtained from density contrast SV-AUC experiments. FIG. 1B (right) is a diagram showing plots of the residual sums of squares of the sedimentation coefficients obtained by varying the partial specific volume under each buffer solution condition.

FIG. 3A is a diagram showing sedimentation coefficient distributions of AAV5 samples based on absorbance measurement at 230 nm. FIG. 3B is a diagram showing sedimentation coefficient distributions of AAV5 samples based on absorbance measurement at 260 nm.

FIG. 9A is a table summarizing calculated values of the molecular weight, the partial specific volume, the s value, and the number of nucleotides for each combination of $n_{capside}$ and $n_{ssDNA}$ calculated by using the molecular weight, the partial specific volume, and $f/f_0$ (=1.32) determined by the AUC experiments of AAV5-EP and AAV5-FP. $f/f_0$ of a dimer and a triangular trimer was calculated by SEDFIT using s values calculated according to the literature (De La Torre J G, Bloomfield VA. Hydrodynamic properties of complex, rigid, biological macromolecules: Theory and applications. Q Rev Biophys. 1981; 14(1):81-139) and the molecular weights determined by AUC experiments. FIG. 9B is a graph showing the correlation between the number of nucleotides and the s value for each association state. The plots in FIG. 9B used the values obtained in FIG. 9A. FIG. 9C is a scatter diagram showing the correlation between the number of nucleotides encapsulated within a capsid and the sedimentation coefficient. White marks and gray marks represent samples from different lots.

FIG. 12 is a workflow diagram for characterizing AAV-EP, AAV-FP, and impurities by SV-AUC with a plurality of measurement wavelengths and refractive index detection.

DESCRIPTION OF EMBODIMENTS

Definitions

Figures 2A, 2B, 2C, 2D:
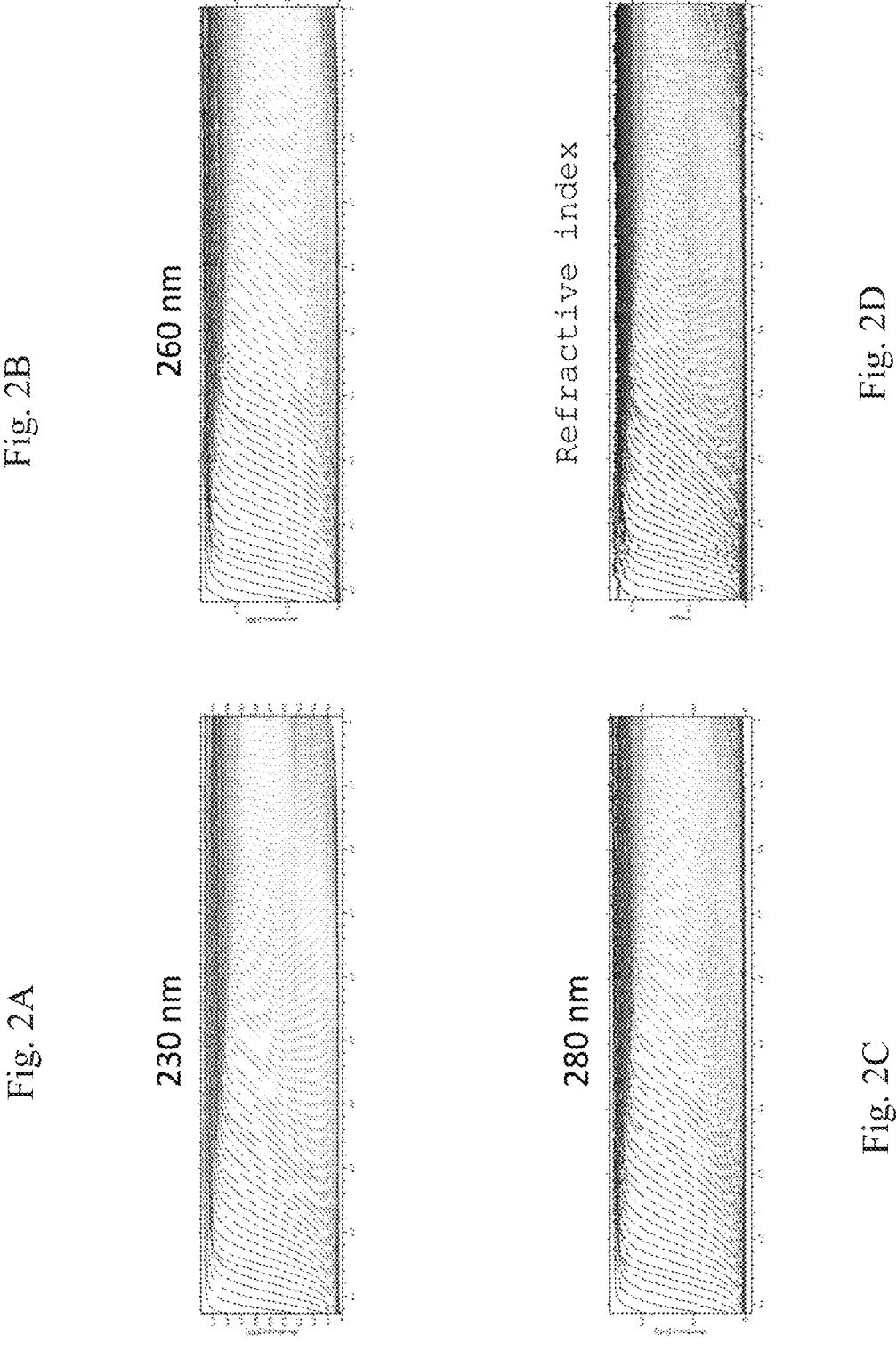
FIG. 2A is a diagram showing a time-dependent intracell concentration distribution based on the absorbance at 230 nm.
FIG. 2B is a diagram showing a time-dependent intracell concentration distribution based on the absorbance at 260 nm.
FIG. 2C is a diagram showing a time-dependent intracell concentration distribution based on the absorbance at 280 nm.
FIG. 2D is a diagram showing a time-dependent intracell concentration distribution based on the refractive index.

As used herein, "molecule delivery particle" means a small object comprising a coat capable of delivering a molecule. The particle size of the molecule delivery particle may be, for example, 5 nm to 10,000 nm, 10 nm to 5,000 μm, 20 nm to 1,000 nm, or 30 nm to 500 nm. The molecule delivery particle may be, for example, a virus particle, a liposome, an albumin particle, a micelle, or a polylactic acid-glycolic acid copolymer (also referred to as "PLGA") particle. The molecule delivery particle can be used in a drug delivery system. When the molecule delivery particle is a virus particle, the particle can be used, for example, for gene therapy or as a virus vector vaccine. The virus may be an adeno-associated virus (AAV), an adenovirus, a herpes virus, a Sendai virus, a stealth virus, a lentivirus, or a retrovirus. The molecule delivery particle can be prepared according to a known method. In one example, the molecule delivery particle may be a recombinant virus particle. The recombinant virus particle can be artificially prepared by using genetic engineering. The molecule delivery particle may be a virus particle produced by using genetic engineering, or may be a virus particle produced in a cultured cell or an egg.

As used herein, "coat" means a structure that separates the inside and the outside of a particle. The coat includes a high molecular weight molecule such as a protein or a lipid. The molecule delivery particle may include, for example; a coat and an interior space defined by the coat. The molecule delivery particle, for example, includes a coat and may include no interior space. The coat of a virus particle or an albumin particle is, for example, substantially composed of a protein. The coat of the virus particle includes, for example, a capsid composed of a protein and optionally further includes an envelope. When the virus particle is an adeno-associated virus (AAV) particle, the coat thereof includes a capsid including three capsid proteins VP1, VP2, and VP3 at a predetermined ratio. The coat of a liposome may include, for example, a lipid bilayer substantially composed of a lipid. The coat of a liposome may include, for example, a lipid bilayer modified with polyethylene glycol (PEG). The coat of a micelle includes, for example, a compound substantially comprising a hydrophilic portion and a hydrophobic portion. The coat of a PLGA particle includes, for example, lactic acid and glycolic acid at a substantially predetermined ratio.

In the molecule delivery particle, the coat includes, for example, substantially the same composition. In one example, when the molecule delivery particle includes a first particle and a second particle, the first particle has a first coat and a first delivery molecule, and the second particle has a second coat, the first coat and the second coat are composed of substantially the same composition. When the molecule delivery particle is a virus particle, the first coat of a first virus particle and the second coat of a second virus particle are each composed of substantially the same protein. When the virus particle is an AAV particle, the first coat of a first AAV particle and the second coat of a second AAV particle are each composed of substantially the same protein including VP1, VP2, and VP3. When the molecule delivery particle is a liposome, the first coat of a first liposome and the second coat of a second liposome each include a lipid bilayer composed of substantially the same lipid component. As used herein, "substantially the same composition" means that a main component is the same. In one example, a substantially identical protein may include a first polypeptide as a main component. In one example, substantially identical protein may include a first polypeptide and a second polypeptide at predetermined proportions as main components. In one example, substantially identical lipid may include a first fatty acid and a second fatty acid at predetermined proportions as main components.

The molecule delivery particle may include a molecule to be delivered (also referred to herein as a "delivery molecule"), for example, on the surface of the coat, in the coat, or inside the coat. As used herein, the "delivery molecule" as used in the context of a molecule delivery particle may be, for example, a polynucleotide, a polypeptide, a protein, a glycoprotein, a lipid, an organic compound, or a radioactive substance, or a combination thereof. The polynucleotide may be, for example, a DNA molecule or an RNA molecule. The DNA molecule or the RNA molecule may be, for example, single-stranded or double-stranded. The polypeptide may be composed of, for example, a natural amino acid or an unnatural amino acid, or a combination thereof. The polypeptide may be, for example, an enzyme or an antibody. The polynucleotide or the polypeptide may be, for example, chemically modified. The organic compound may be, for example, a drug that is used as an anticancer agent. The organic compound may be, for example, one that is used as a nutrient. The radioactive substance may be, for example, strontium chloride and radium chloride. The delivery molecule may be a coat.

The molecule delivery particle may include, for example, two or more types of particles (for example, a first particle and a second particle). When the molecule delivery particle is a virus particle, the virus particle may include, for example, a full virus particle including a capsid, which is a coat, and a genomic DNA molecule thereof, as the first particle and a capsid particle including a capsid but not including the genomic DNA molecule (also referred to herein as an "empty particle") as the second particle. A combination of two or more types of particles included in the molecule delivery particle can be appropriately set according to the purpose. In one example, a full virus particle may be the first particle, a capsid particle may be the second particle, and a further virus particle (for example, a dimer of a full virus particle, a dimer of a capsid particle, a dimer of a full virus particle and a capsid particle, or an aggregate of a virus particle, or a mixture thereof) may be a third particle. For example, when the third particle is a dimer of a full virus particle and a capsid particle, the third particle includes a third coat including two capsids and a third delivery molecule including one genomic DNA. In a further example, a capsid particle may be the first particle, a full virus particle may be the second particle, and a further virus particle may be the third particle.

In the above examples, the types of virus particles have been described, and the particle types are not limited thereto. For example, when the molecule delivery particle is a liposome, the liposome may include a full particle including a lipid bilayer, which is a coat, and an encapsulated molecule as the first particle, and an empty particle including a lipid bilayer but not including the molecule as the second particle. In a further example, the liposome may include a full particle as the first particle, an empty particle as the second particle, and a further particle (for example, an aggregate of a liposome) as the third particle. When the molecule delivery particle is an albumin particle, the albumin particle may include a particle comprising a first molecular weight as the first particle and a particle comprising a second molecular weight as the second particle.

The molecule delivery particle can be used, for example, in order to deliver a molecule to a predetermined location in the body of an animal. The animal may be, for example, a reptile, a bird, or a mammalian animal. The mammalian animal may be, for example, a human or a non-human mammalian animal. The non-human mammalian animal may be, for example, a rodent such as a mouse, a non-human primate such as a chimpanzee, an artiodactyl such as a cow, a perissodactyl such as a horse, or a companion animal such as a dog and a cat. In one embodiment, the mammalian animal is a non-human primate or a human. The predetermined location may be, for example, an organ or a cell of an animal. The predetermined organ may be, for example, a heart, a lung, a liver, a stomach, a pancreas, or a kidney. The predetermined cell may be, for example, a normal cell or an abnormal cell. The normal cell may be, for example, a cardiomyocyte, a hepatocyte, or a blood cell. The abnormal cell may be, for example, a cancer cell.

The molecular weight of the molecule delivery particle can be measured by using a known method such as static light scattering, dynamic light scattering, and a combination of centrifugation and dynamic light scattering. In addition, the molecular weight of the molecule delivery particle may be a known value or a theoretically calculated value. For example, when the particle is an AAV particle, the molecular weight of the capsid of the AAV particle can be calculated based on the amino acid composition of each of the three structural proteins (VP1, VP2, and VP3) and the ratio of those structural proteins. A recombinant AAV includes, for example, genomic RNA modified to serve a predetermined purpose. The molecular weight of the modified genomic RNA molecule can be calculated based on the designed nucleotide sequence. The molecular weight of the recombinant AAV can be calculated by adding the molecular weight of the capsid and the molecular weight of the genomic RNA molecule. In a further example, the molecular weight of the molecule delivery particle can be determined, for example, according to a known method for determining the molecular weight or a method disclosed herein (for example, "Method for characterizing molecule delivery particle including determining molecular weight" described later).

As used herein, "optical measurement" means a method that can irradiate a subject to be measured with light to acquire optical data in which an optical signal from the subject to be measured is recorded. The optical measurement can be carried out by optical measurement means. The optical measurement means may include, for example, a light emission apparatus, a photodetection apparatus, and an apparatus that can record and output optical data. The light emission apparatus can, for example, emit light of one or more wavelengths according to the purpose. The light emission apparatus includes a light source such as a light emitting diode, laser light, a xenon lamp, and a halogen lamp, and optionally a spectroscope for separating light of a predetermined wavelength or an optical filter for transmitting or reflecting a predetermined wavelength. The photodetection apparatus may include, for example, a photomultiplier tube, a silicon photodiode, or an avalanche photodiode (APD), or a combination thereof. The photodetection apparatus may include, for example, an interferometer, a differential refractive index detector (RID), a spectrophotometer, or an absorption spectrometer, or a combination thereof. The apparatus that can record and output optical data may be, for example, a hard disk drive (HDD) or a solid-state drive (SSD). The optical measurement means may be a one-unit apparatus in which a photodetection apparatus, a light emission apparatus, and an apparatus that can record and output optical data are integrated, or a multi-unit apparatus in which those apparatuses are separated. Such a one-unit apparatus or multi-unit apparatus is commercially available.

The wavelength used for optical measurement can be set, for example, according to the molecule delivery particle. As the wavelength used for optical measurement, for example, a maximum absorption wavelength of a coat component constituting the molecule delivery particle or a molecule to be delivered and/or a wavelength therearound may be used. In optical measurement, light of one or more measurement wavelengths may be used according to the purpose. For example, the light of 1, 2, 3, 4, 5, 6, 7, 8, 9, 10, 11, or more wavelengths may be used in optical measurement. In one example, light of 5, 7, 9, 11, or 13 wavelengths is used in optical measurement. In one example, light of 9, 11, or 13 wavelengths is used in optical measurement.

As used herein, "optical data" means information including a record of an optical signal measured by irradiating a subject to be measured with light. The optical data includes, for example, data about transmitted light, scattered light, reflected light, absorption, refractive index, or absorbance, or a combination thereof. In one example, the optical data includes data about absorbance (referred to herein as "absorbance data") and data about refractive index (referred to herein as "refractive index data"). The refractive index data can be obtained, for example, by using an interferometer. The absorbance data can be obtained, for example, by using an absorption spectrometer. When optical measurement is carried out a predetermined number of times at predetermined time intervals, the optical data may include measurement time information and data for the predetermined number of times. When optical measurement is carried out by using a plurality of measurement wavelengths, the optical data may include optical data for each wavelength of the plurality of measurement wavelengths.

As used herein, "particle separation" means a method for making each type of particle distinguishable from a particle population, including two or more types of particles. The particle separation may be a method for making a peak in a distribution of each type of particle distinguishable from a particle population including two or more types of particles, for example, based on a particle property. The particle separation may be, for example, chromatography (for example, ion exchange chromatography, size exclusion chromatography, or affinity chromatography, or a combination thereof), centrifugation, or field flow fractionation (FFF). As used herein, ultracentrifugation is centrifugation that produces an acceleration of 10,000 G or more. The particle separation can be applied to a particle population including one type of particle, a particle population including two types of particles, or a particle population including three or more types of particles. In one example, the particle groups that are distinguishably separated by particle separation may be designated as the first particle, the second particle, and the like in descending order of number. In a further example, among the particle groups distinguishably separated by particle separation, a particle exhibiting a value close to a predetermined physical quantity, such as a sedimentation coefficient, may be designated the first particle. The molecule delivery particle is dissolved or dispersed in a solvent suitable for a method of particle separation. A solution or a dispersion containing a molecule delivery particle is subjected to particle separation with optical measurement. The particle separation can be carried out by using particle separation means. The particle separation means may be, for example, a centrifugal apparatus or a chromatographic apparatus (for example, HPLC). In one embodiment, the particle separation is centrifugation. In one embodiment, the particle separation is chromatography. In one embodiment, the particle separation is FFF.

"Particle separation with optical measurement" includes carrying out optical measurement during particle separation or after particle separation. In one example, when the molecule delivery particle is subjected to centrifugation, optical measurement may be carried out on the molecule delivery particle during centrifugation. In one example, when the molecule delivery particle is subjected to chromatography, optical measurement may be carried out on a droplet or a divided solution including the molecule delivery particle that has been chromatographically fractionated. "Centrifugation with optical measurement" as used in the context of the "Method for characterizing molecule delivery particle including determining molecular weight" described later includes carrying out optical measurement during centrifugation of a molecule delivery particle including one type of particle.

The particle separation with optical measurement can be carried out by using particle separation means including optical measurement means. The particle separation means including optical measurement means may be, for example, a one-unit apparatus in which particle separation means and optical measurement means are integrated, or a two-unit or three- or more unit apparatus in which particle separation means and optical measurement means are separated. In the particle separation means including optical measurement means, optical data may be acquired by using the optical measurement means while or after the molecule delivery particle is separated into the type thereof by the particle separation means. The particle separation with optical measurement may be, for example, centrifugation or chromatography with optical measurement.

The "particle property" as used in the context of particle separation may be, for example, a molar extinction coefficient, diffusion coefficient, a sedimentation coefficient, or a bulk property (for example, particle size, shape, molecular weight, density, or partial specific volume), or a combination thereof. A particle property can be obtained directly or indirectly from optical data (for example, refractive index data or absorbance data, or a combination thereof) obtained by subjecting the molecule delivery particle to particle separation with optical measurement. When the particle separation is centrifugation, the particle in a solution sediments in the centrifugal direction in which a centrifugal force is applied, and a moving boundary surface is formed between a region in which the particle no longer exists in the solution and a region in which the particle still exists. The shape and the change over time of this moving boundary surface reflect the particle's sedimentation coefficient and diffusion coefficient. From the sedimentation coefficient and the diffusion coefficient of the particle, the molecular weight of the particle can be calculated by using a known relational expression, for example, Equation (3). Information about a moving boundary surface is included, for example, in refractive index data and absorbance data. In a further example, the molar concentration of the particle can be obtained from refractive index data. In a further example, the molar extinction coefficient of the particle can be obtained from refractive index data and absorbance data.

As used herein, "increment in refractive index" refers to a change in the refractive index n of a solution including a molecule delivery particle. In one example, the method disclosed herein determines an increment in refractive index for each type of particle included in the molecule delivery particle. In one example, an increment in refractive index is determined for a mixture of one particle type and a further particle type included in the molecule delivery particle.

As used herein, the "specific refractive index increment" means the proportion of a change in refractive index n to a change in particle concentration c of a solution including a molecule delivery particle, and is expressed, for example, as a differential coefficient do/dc. In one example, a specific refractive index increment is determined for each type of particle included in the molecule delivery particle by the method disclosed herein. In one example, a refractive index change value is determined for a mixture of one particle type and a further particle type included in the molecule delivery particle.

As used herein, "absorbance" is a value that represents the degree to which the intensity of light is attenuated when measurement light passes through a molecule delivery particle. In one example, an absorbance is determined for each type of particle included in the molecule delivery particle by the method disclosed herein. In one example, an absorbance is determined for a mixture of one particle type and a further particle type included in the molecule delivery particle.

As used herein, "molar concentration" is a value that represents the concentration of a molecule delivery particle in a unit volume of a solution. In one example, a molar concentration is determined for each type of particle included in the molecule delivery particle by the method disclosed herein. In one example, a molar concentration is determined for a mixture of one particle type and a further particle type included in the molecule delivery particle.

As used herein, "partial specific volume" is an increase in the volume of a solution when 1 gram of a molecule delivery particle is dissolved in a large amount of solvent. The partial specific volume corresponds approximately to the reciprocal of density. In one example, a partial specific volume is determined for each type of particle included in the molecule delivery particle by the method disclosed herein. In one example, a partial specific volume is determined for a mixture of one particle type and a further particle type included in the molecule delivery particle.

As used herein, "molar extinction coefficient" is the optical density of a 1 M solution per cm of an optical path. In one example, a molar extinction coefficient is determined for each component of a particle included in the molecule delivery particle by the method disclosed herein. For example, when the molecule delivery particle includes a first particle and a second particle, the first particle has a first coat and a first delivery molecule, and the second particle has a second coat, a molar extinction coefficient is determined for each of the first coat, the second coat, and the first delivery molecule.

As used herein, "isosbestic point" means the wavelength of light at which two or more target substances exhibit the same absorbance or molar extinction coefficient. In one example, when the molecule delivery particle includes a first particle and a second particle, the first particle includes a first coat and a first delivery molecule, and the second particle has a second coat, the isosbestic point may be the wavelength at which the molar extinction coefficient of the first delivery molecule and the molar extinction coefficient of the second coat are consistent with each other. In one example, the method disclosed herein can identify the isosbestic point. Specifically, the isosbestic point can be determined, for example, by subjecting the molecule delivery particle including the first particle and the second particle to particle separation with optical measurement as disclosed herein, determining molar extinction coefficients of each of the first delivery molecule and the second particle at a plurality of measurement wavelengths, and identifying the intersection of a fitted curve of the molar extinction coefficients of the first delivery molecule at the plurality of measurement wavelengths and a fitted curve of the molar extinction coefficients of the second particle at the plurality of measurement wavelengths.

As used herein, "quantitative ratio" represents the proportion of the quantity of a further substance to the quantity of a predetermined substance. In one example, when the molecule delivery particle includes a first particle and a second particle, the quantitative ratio may be the ratio of the quantity of the second particle to the quantity of the first particle. In one example, the quantitative ratio may be the ratio of the number of the second particle to the number of the first particle. In one example, the quantitative ratio may be the ratio of the numbers of a mixture of a further particle type to one particle type included in the molecule delivery particle. In one example, when the molecule delivery particle includes a first particle, a second particle, and a third particle, the quantitative ratio may be the percentage (%) of the quantity of the first particle to the quantity of the molecule delivery particle (quantity of first particle+quantity of second particle+quantity of third particle).

The "solvent" used in the context of the first solution described later can be used without particular limitation as long as it is compatible with the molecule delivery particle. The solvent may be, for example, light water ($H_2O$). The "isotopically labeled solvent" used in the context of the second solution described later has the same chemical formula as that of the solvent, but one or more elements are replaced with a corresponding isotope of the element. The isotope may be, for example, a non-radioactive isotope or a radioactive isotope, and is preferably a non-radioactive isotope. Isotopic replacement may be, for example, replacing a hydrogen atom $^1H$ with a deuterium atom $^2H$ or replacing an oxygen atom $^{16}O$ with $^{18}O$. When the solvent is light water ($H_2O$), the isotopically labeled solvent may be $H_2{}^{18}O$. The first solution may further include an isotopically labeled solvent at a first ratio in addition to the solvent. The first ratio of the isotopically labeled solvent to the solvent (isotopically labeled solvent: solvent) may be, for example, 0:100 or 10:90. The second solution may further include a solvent at a second ratio in addition to the isotopically labeled solvent. The first ratio and the second ratio are different from each other. The first ratio of the isotopically labeled solvent to the solvent (isotopically labeled solvent: solvent) may be, for example, 35:65 or 60:40. The first solution and the second solution may further include a buffering agent such as phosphoric acid or a salt thereof, or an inorganic salt such as sodium chloride.

Method for Characterizing Molecule Delivery Particle Including Determining Molecular Weight One aspect of the present invention provides a method for characterizing a molecule delivery particle including determining a molecular weight. In one embodiment, the method includes: subjecting a first solution including a molecule delivery particle and a solvent to centrifugation with optical measurement to determine a sedimentation coefficient of the molecule delivery particle in the first solution; and subjecting a second solution including a molecule delivery particle and an isotopically labeled solvent to centrifugation with optical measurement to determine a sedimentation coefficient of the molecule delivery particle in the second solution.

The step of determining a sedimentation coefficient of the molecule delivery particle in the first solution and the step of determining a sedimentation coefficient of the molecule delivery particle in the second solution may be carried out simultaneously or sequentially. In one embodiment, the two steps are carried out simultaneously.

By subjecting a first solution including a molecule delivery particle and a solvent to centrifugation with optical measurement, optical data (including, for example, absorbance data) of the first solution is obtained. From the optical data, the sedimentation coefficient of the molecule delivery particle in the first solution is determined according to the method described in the Examples. Specifically, from the optical data, for example, by using a commercially available program (for example, the program GUSSI or Microsoft Excel), the sedimentation coefficient distribution of the molecule delivery particle in the first solution is obtained, and a known model formula (for example, the c(s) distribution model of the program SEDFIT) is globally fitted to determine the sedimentation coefficient of the molecule delivery particle in the first solution. Similarly, by subjecting a second solution including a molecule delivery particle and an isotopically labeled solvent to centrifugation with optical measurement, optical data (including, for example, absorbance data) of the second solution is obtained, and from the optical data, the sedimentation coefficient of the molecule delivery particle in the second solution is determined.

For example, when the molecule delivery particle is a virus particle, the sedimentation coefficient determined by the present method can be compared with the sedimentation coefficient calculated from the molecular weight of the molecule delivery particle, the friction coefficient ratio ($f/f_0$), the partial specific volume, the solvent density, and the solvent viscosity. The method for calculating the sedimentation coefficient from the friction coefficient, the solvent density, and the solvent viscosity is known, and, for example, Analytical Ultracentrifugation Instrumentation, Software, and Applications can be referred to.

The method for characterizing a molecule delivery particle including determining a molecular weight further includes a step of determining a partial specific volume of the molecule delivery particle based on the sedimentation coefficient of the molecule delivery particle in the first solution and the sedimentation coefficient of the molecule delivery particle in the second solution. The partial specific volume of the molecule delivery particle can be determined according to the method described in the Examples. Specifically, a known model formula (for example, the "Hybrid Global Discrete Species Global Continuous Distribution" model of SEDPHAT) is fitted globally to the sedimentation profiles (for example, a time-dependent intracellular concentration distribution shown in FIG. 2) of the molecule delivery particle in the first solution and the second solution to determine the partial specific volume.

When the molecule delivery particle is an empty particle, the partial specific volume of the empty particle can be obtained by using the molecular weight calculated from the amino acid composition and the program SEDNTERP. When the molecule delivery particle is a full particle, the partial specific volume of the full particle can be calculated by using equation 1.

The method for characterizing a molecule delivery particle including determining a molecular weight further includes a step of determining a molecular weight of the molecule delivery particle based on the sedimentation coefficient of the molecule delivery particle in the first solution, the sedimentation coefficient of the molecule delivery particle in the second solution, and the partial specific volume of the molecule delivery particle. The method for determining a molecular weight based on the sedimentation coefficient and the partial specific volume is known, and, for example, the Protein Science Society Archive, 1, e043 (2008) (http://www.pssj.jp/archives/protocol/measurement/XLA_01/XLA_01.html) and Analytical Ultracentrifugation Instrumentation, Software, and Applications can be referred to. Specifically, the molecular weight of the molecule delivery particle can be calculated by substituting the sedimentation coefficient and the partial specific volume of the particle into the following numerical expression.

$$s = M(1 - vbar \cdot \rho)/Nf \qquad \text{[Equation 1]}$$

where s is the sedimentation coefficient of the particle, M is the molecular weight of the particle, vbar is the partial specific volume of the particle, $\rho$ is the solvent density, N is Avogadro's number, and f is the friction coefficient. The friction coefficient f can be calculated from the following numerical expression.

$$f = 6\pi\eta R_s \qquad \text{[Equation 2]}$$

where $\eta$ is the solvent viscosity and Rs is the particle size. The particle size Rs can be calculated from the following equation.

$$vbar = \frac{3}{4}\pi R_s^3 \qquad \text{[Equation 3]}$$

In one embodiment, the method for characterizing a molecule delivery particle includes: determining, from optical data (including absorbance data) of a first solution including a molecule delivery particle and a solvent obtained by centrifugation with optical measurement, a sedimentation coefficient of the molecule delivery particle in the first solution; determining, from optical data (including absorbance data) of a second solution including a molecule delivery particle and an isotopically labeled solvent obtained by centrifugation with optical measurement, a sedimentation coefficient of the molecule delivery particle in the second solution; determining a partial specific volume of the molecule delivery particle based on the sedimentation coefficient of the molecule delivery particle in the first solution and the sedimentation coefficient of the molecule delivery particle in the second solution; and determining a molecular weight of the molecule delivery particle based on the sedimentation coefficient of the molecule delivery particle in the first solution, the sedimentation coefficient of the molecule delivery particle in the second solution, and the partial specific volume of the molecule delivery particle.

According to the method for determining a molecular weight in the present aspect, even in the case of a molecule delivery particle whose molecular weight is unknown, a molecule delivery particle whose molecular weight is theoretically difficult to calculate (for example, a naturally occurring inactivated virus or attenuated virus, or a lipid nanoparticle (LNP) comprising mRNA encapsulated in a lipid), the molecular weight thereof can be determined. In addition, according to the method for determining a molecular weight in the present embodiment, the molecular weight can be determined together with a further property of the particle in centrifugation with optical measurement.

In the optical measurement in the method for characterizing a molecule delivery particle including determining a molecular weight, data about the absorbance of the molecule delivery particle and optionally further optical data are acquired, for example, by using one or more measurement wavelengths. In the optical measurement, for example, one wavelength may be used. For example, an analytical ultra-centrifuge OPTIMA (Beckman Coulter, Inc., USA) can be used in centrifugation with optical measurement according to the method.

Method for Characterizing Molecule Delivery Particle Including Determining Molar Concentration One aspect of the present invention provides a method for characterizing a molecule delivery particle including determining a molar concentration. In one embodiment, the method includes: subjecting a molecule delivery particle including a first particle and a second particle to particle separation with optical measurement to determine an increment in refractive index of each of the first particle and the second particle; and determining a molar concentration of each of the first particle and the second particle based on the increment in refractive index, a molecular weight, and a specific refractive index increment of each of the first particle and the second particle.

By subjecting a molecule delivery particle including a first particle and a second particle to particle separation with optical measurement, optical data (including, for example, refractive index data) of the molecule delivery particle is obtained, and the first particle and the second particle are separated so as to be distinguishable. The optical data includes information about the increment in refractive index of each of the first particle and the second particle. From the optical data, the increment in refractive index of each of the first particle and the second particle can be determined, for example, according to the method described in the Examples. Specifically, the increment in refractive index of each of the first particle and the second particle can be determined by using a program available commercially or for free (for example, Microsoft Excel or the program GUSSI) after analyzing the optical data with, for example, the program SEDFIT to obtain a sedimentation coefficient distribution of the molecule delivery particle or a peak area of an eluted component. The sedimentation coefficient distribution can be obtained, for example, by centrifugation with optical measurement. The peak area of an eluted component can be obtained, for example, by chromatography with optical measurement.

In the step of determining a molar concentration, the respective molar concentrations of the first particle and the second particle can be determined by dividing the respective increments in refractive index ($\delta$d) of the first particle and the second particle by the respective specific refractive index increments (dn/dc) thereof, which are refractive index change values per concentration, to obtain respective gram concentrations thereof, and further dividing the gram concentrations by the respective molecular weight thereof.

The specific refractive index increment (dn/dc) of each of the first particle and the second particle can be determined, for example, according to the method described in the Examples or a known method. Specifically, do/dc can be determined from the amino acid composition of the particles by using SEDFIT. Alternatively, a known value may be used for the specific refractive index increment of each of the first particle and the second particle. For example, as the specific refractive index increments of a phospholipid and a lipid, values disclosed in Optical characterization of liposomes by right-angle light scattering and turbidity" Biochimica et Biophysica Acta (BBA)—Biomembranes 1467, 1, 219-226 (2000) can be used. In addition, the specific refractive index change of a component such as a phospholipid or a lipid takes almost the same value as that of the specific refractive index change of a protein, and thus a specific refractive index increment determined for a protein can be used.

The respective molar concentrations of the first particle and the second particle can be determined, for example, by using the respective molecular weights determined according to the "Method for characterizing molecule delivery particle including determining molecular weight" described above, or optionally by using the respective molecular weights theoretically estimated from the respective compositions of the first particle and the second particle.

In one embodiment, the method for characterizing a molecule delivery particle including determining a molar concentration includes: determining, from refractive index data of the molecule delivery particle obtained by particle separation with optical measurement, an increment in refractive index of each of the first particle and the second particle; and determining a molar concentration of each of the first particle and the second particle based on the increment in refractive index, a molecular weight, and a specific refractive index increment of each of the first particle and the second particle.

In the above embodiment, a molecule delivery particle including a first particle and a second particle was given as an example, but the molecule delivery particle used in the present aspect is not limited thereto. The molecule delivery particle used in the present aspect may include three types of particles (for example, first particle, second particle, and third particle) or four or more types of particles.

In one embodiment, the first particle includes a first coat and a first delivery molecule, and the second particle includes a second coat. In one example, the second coat includes substantially the same composition as that of the first coat. In one example, the second particle does not include a delivery molecule. In one embodiment, the first particle includes a first coat and a first delivery molecule, and the second particle includes a second coat composed of substantially the same composition as that of the first coat but does not include a delivery molecule. In one example, when the molecule delivery particle includes a third particle, the third particle includes a third coat composed of substantially the same composition as that of the first coat, and includes a third delivery molecule comprising substantially the same composition as that of first delivery molecule. In one example, when the molecule delivery particle is a virus particle, the first virus particle includes a capsid as the first coat and includes a first polynucleotide of a predetermined chain length as the first delivery molecule. In this example, the second virus particle includes the capsid as the second coat, but does not include a polynucleotide as a delivery molecule. In this example, the third virus particle includes, for example, the capsid as the third coat, and may include a third polynucleotide of a shorter chain length than that of the first polynucleotide as the third delivery molecule. In a further example, the third virus particle may be, for example, an aggregate of virus particles, and the aggregate of virus particles includes, for example, three of the capsids as the third coat, and may include a third polynucleotide of a total chain length greater than the chain length of the first polynucleotide as the third delivery molecule.

In the optical measurement in the method, data about the refractive index of the molecule delivery particle, and optionally further optical data are acquired, for example, by using one or more measurement wavelengths. In the optical measurement, for example, one wavelength may be used. For example, an analytical ultracentrifuge OPTIMA (Beckman Coulter, Inc., USA) can be used in the centrifugation with optical measurement according to the method.

Method for Characterizing Molecule Delivery Particle Including Determining Molar Extinction Coefficient One aspect of the present invention provides a method for characterizing a molecule delivery particle including determining a molar extinction coefficient. In one embodiment, the method includes: subjecting a molecule delivery particle including a first particle and a second particle to particle separation with optical measurement at a plurality of measurement wavelengths to determine an absorbance of each of the first particle and the second particle for each measurement wavelength of the plurality of measurement wavelengths; and determining a molar extinction coefficient of each of the first particle and the second particle for the each measurement wavelength based on the absorbance of each of the first particle and the second particle and the molar concentration of each of the first particle and the second particle.

By subjecting a molecule delivery particle including a first particle and a second particle to particle separation with optical measurement at a plurality of measurement wavelengths, optical data (including, for example, absorbance data) of the molecule delivery particle is obtained, and the first particle and the second particle are separated so as to be distinguishable. The optical data includes information about the absorbance of each of the first particle and the second particle for each measurement wavelength. From the optical data, the absorbance of each of the first particle and the second particle is determined for each measurement wavelength according to the method described in the Examples. Specifically, from optical data at a certain measurement wavelength among the optical data, for example, by using a commercially available program (for example, the program GUSSI), the sedimentation coefficient distribution of the molecule delivery particle is obtained, and a known model formula (for example, the c(s) distribution model of the program SEDFIT) is globally fitted to determine the absorbance of each of the first particle and the second particle at the measurement wavelength. The determined respective absorbances of the first particle and the second particle correspond to the peak areas of the respective peaks corresponding to the first particle and the second particle observed in the sedimentation coefficient distribution. By processing the optical data at the other measurement wavelengths in the same manner, the absorbance of each of the first particle and the second particle is determined for each of the plurality of measurement wavelengths used.

The molar concentration of each of the first particle and the second particle used in the step of determining a molar extinction coefficient can be obtained by using the "Method for characterizing molecule delivery particle including determining molar concentration" described above. In this step, by dividing the absorbance of the first particle at a certain measurement wavelength by the molar concentration of the first particle, the molar extinction coefficient of the first particle at the wavelength can be obtained. Similarly, by dividing the absorbance of the second particle at the measurement wavelength by the molar concentration of the second particle, the molar extinction coefficient of the second particle at the wavelength can be obtained. By processing the optical data at the other measurement wavelengths in the same manner, the molar extinction coefficient of each of the first particle and the second particle is determined for each of the plurality of measurement wavelengths used.

In one embodiment, the method for characterizing a molecule delivery particle including determining a molar extinction coefficient includes: subjecting a molecule delivery particle including a first particle and a second particle to particle separation with optical measurement to determine an increment in refractive index of each of the first particle and the second particle for a particular wavelength; determining an absorbance of each of the first particle and the second particle for each of a plurality of measurement wavelengths; determining a molar concentration of each of the first particle and the second particle based on the increment in refractive index, a molecular weight, and a specific refractive index increment of each of the first particle and the second particle; and determining a molar extinction coefficient of each of the first particle and the second particle for each of the measurement wavelengths based on the absorbance of each of the first particle and the second particle and the molar concentration of each of the first particle and the second particle. In the embodiment, the particle separation with optical measurement to determine an increment in refractive index and the particle separation with optical measurement to determine an absorbance may be carried out simultaneously or sequentially. In one embodiment, the two particle separations with optical measurement are carried out simultaneously.

In one embodiment, the method for characterizing a molecule delivery particle including determining a molar extinction coefficient includes: determining, from refractive index data of the molecule delivery particle obtained by particle separation with optical measurement, an increment in refractive index of each of the first particle and the second particle; determining a molar concentration of each of the first particle and the second particle based on the increment in refractive index, a molecular weight, and a specific refractive index increment of each of the first particle and the second particle; determining, from absorbance data of the molecule delivery particle obtained by particle separation with optical measurement at a plurality of measurement wavelengths, an absorbance of each of the first particle and the second particle for each measurement wavelength of the plurality of measurement wavelengths; and determining a molar extinction coefficient of each of the first particle and the second particle for the each measurement wavelength based on the absorbance of each of the first particle and the second particle and the molar concentration of each of the first particle and the second particle. The refractive index data and the absorbance data may be stored in one optical data, or may be stored in two different optical data, respectively. In one embodiment, the two data are stored in one optical data.

In the above embodiment, a molecule delivery particle including a first particle and a second particle was given as an example, but the molecule delivery particle used in the present aspect is not limited thereto. The molecule delivery particle used in the present aspect may include three types of particles (for example, first particle, second particle, and third particle) or four or more types of particles.

In the optical measurement in the method, data about the absorbance of the molecule delivery particle, and optionally further optical data are acquired by using a plurality of measurement wavelengths. For example, the optical measurement may use light of 2, 3, 4, 5, 6, 7, 8, 9, 10, 11, 12, or more wavelengths. In one example, light of 5, 7, 9, 11, or 13 wavelengths is used in optical measurement. A further example uses light of 9, 11, or 13 wavelengths. For example, an analytical ultracentrifuge OPTIMA (Beckman Coulter, Inc., USA) can be used in the centrifugation with optical measurement according to the method.

Method for Characterizing Molecule Delivery Particle Including Determining Molar Extinction Coefficient of First Delivery Molecule One aspect of the present invention provides a method for characterizing a molecule delivery particle including determining a molar extinction coefficient of a first delivery molecule. In the method, a molecule delivery particle including a first particle and a second particle wherein the first particle has a first coat and a first delivery molecule, and the second particle has a second coat can be used. In one example, the first particle includes a first coat and a first delivery molecule, and the second particle includes a second coat comprising substantially the same composition as that of the first coat but does not include a delivery molecule. The method includes: determining a molar extinction coefficient of each of the first particle and the second particle for each measurement wavelength based on the absorbance of each of the first particle and the second particle and a molar concentration of each of the first particle and the second particle; and determining a molar extinction coefficient of the first delivery molecule for each measurement wavelength by subtracting the molar extinction coefficient of the second particle from the molar extinction coefficient of the first particle. The molar concentration of each of the first particle and the second particle can be determined according to the "Method for characterizing molecule delivery particle including determining molar concentration" described above. The molar extinction coefficient of each of the first particle and the second particle can be determined according to the "Method for characterizing molecule delivery particle including determining molar extinction coefficient" described above.

The first particle and the second particle include a first coat and a second coat comprising substantially the same composition, respectively. The coats comprising substantially the same composition may be, for example, proteinaceous (for example, capsid protein or albumin) coats, lipid bilayer coats, or polymer (for example, PEG or PLGA) coats. The coat of each particle preferably has the same composition and the same size. As one example of the coat, when the molecule delivery particle is a virus particle, the coat is substantially the same proteinaceous capsid and has substantially the same size (for example, capsid monomer). In one example, the first particle includes a first delivery molecule, and the second particle does not include a delivery molecule. For example, when the molecule delivery particle is a virus particle, the first delivery molecule may be a nucleic acid (for example, DNA or RNA) delivery molecule. In the above example, a virus particle was given as an example of the molecule delivery particle, but the molecule delivery particle is not limited thereto. For example, when the molecule delivery particle is a liposome, the first delivery molecule may include a drug component (for example, anticancer agent) or a nutrient as a delivery molecule.

Specifically, the method includes carrying out the "Method for characterizing molecule delivery particle including determining molar concentration" and the "Method for characterizing molecule delivery particle including determining molar extinction coefficient" described above on a molecule delivery particle including a first particle and a second particle to determine a molar concentration and a molar extinction coefficient of each of the first particle and the second particle for each measurement wavelength. Next, by subtracting the molar extinction coefficient of the second particle (comprising a second coat) determined for a certain measurement wavelength from the molar extinction coefficient of the first particle (comprising a first coat and a first delivery molecule) determined for the measurement wavelength, the molar extinction coefficient of the first delivery molecule at the measurement wavelength can be obtained. By processing the other measurement wavelengths in the same manner, the molar extinction coefficient of the first delivery molecule is determined for each of the plurality of measurement wavelengths used.

More specifically, the method includes subjecting a molecule delivery particle including a first particle and a second particle to particle separation with optical measurement at a plurality of measurement wavelengths to determine an increment in refractive index and an absorbance of each of the first particle and the second particle for each measurement wavelength of the plurality of measurement wavelengths. Next, the method includes determining a molar concentration of each of the first particle and the second particle based on the determined increment in refractive index, a molecular weight, and a specific refractive index increment of each of the first particle and the second particle. Further, the method includes determining a molar extinction coefficient of each of the first particle and the second particle for the each measurement wavelength based on the absorbance of each of the first particle and the second particle and the molar concentration of each of the first particle and the second particle. Additionally, the method includes determining a molar extinction coefficient of the first delivery molecule for each measurement wavelength by subtracting the molar extinction coefficient of the second particle from the molar extinction coefficient of the first particle. The particle separations with optical measurement to determine an increment in refractive index and an absorbance described above may be carried out simultaneously or sequentially. In one embodiment, the particle separations with optical measurement described above are carried out simultaneously.

In one embodiment, when the first particle is a full virus particle comprising a capsid and genomic DNA, and the second particle is an empty virus particle comprising a capsid, the molar extinction coefficient of the genomic DNA can be determined by subtracting the molar extinction coefficient of the empty virus particle from the molar extinction coefficient of the full virus particle based on the above method. In the above embodiment, a full virus particle and an empty virus particle were used as molecule delivery particles, but the first particle and the second particle are not limited thereto. In a further example, a full liposome particle that includes a lipid bilayer as a coat and a drug encapsulated therein, and an empty liposome particle that includes a lipid bilayer but does not include a drug can be used as molecule delivery particles.

In one embodiment, the method for characterizing a molecule delivery particle including determining a molar extinction coefficient of a first delivery molecule includes: determining, from optical data (including, for example, absorbance data and refractive index data) of the molecule delivery particle obtained by particle separation with optical measurement at a plurality of measurement wavelengths, wherein the first particle has a first coat and a first delivery molecule, and the second particle has a second coat, an increment in refractive index and an absorbance of each of the first particle and the second particle for each measurement wavelength of the plurality of measurement wavelengths; determining a molar concentration of each of the first particle and the second particle based on the increment in refractive index, a molecular weight, and a specific refractive index increment of each of the first particle and the second particle; determining a molar extinction coefficient of each of the first particle and the second particle for the each measurement wavelength based on the absorbance of each of the first particle and the second particle and the molar concentration of each of the first particle and the second particle; and determining a molar extinction coefficient of the first delivery molecule for each measurement wavelength by subtracting the molar extinction coefficient of the second particle from the molar extinction coefficient of the first particle.

In the above embodiment, a molecule delivery particle including a first particle and a second particle was given as an example, but the molecule delivery particle used in the present aspect is not limited thereto. The molecule delivery particle used in the present aspect may include three types of particles (for example, first particle, second particle, and third particle) or four or more types of particles.

Method for Characterizing Molecule Delivery Particle Including Determining Quantitative Ratio One aspect of the present invention provides a method for characterizing a molecule delivery particle including determining a quantitative ratio. In the method, a molecule delivery particle including a first particle and a second particle wherein the first particle has a first coat and a first delivery molecule, and the second particle has a second coat can be used. In one example, the second particle does not include a delivery molecule.

(1) Method for Characterizing Molecule Delivery Particle Including Determining Isosbestic Point and Determining Quantitative Ratio The method according to one embodiment includes: identifying an isosbestic point at which the molar extinction coefficient of the second particle and the molar extinction coefficient of the first delivery molecule are consistent with each other; and determining a quantitative ratio between the first particle and the second particle by using an absorbance of each of the first particle and the second particle at the isosbestic point. The molar extinction coefficient of each of the second particle and the first delivery molecule can be determined according to the "Method for characterizing molecule delivery particle including determining molar extinction coefficient of first delivery molecule" described above. The absorbance of each of the first particle and the second particle at the isosbestic point can be determined according to the method described in the Examples or the "step of determining an absorbance" in the "Method for characterizing molecule delivery particle including determining molar extinction coefficient" described above. In the present embodiment, the molecule delivery particle used to identify an isosbestic point and the molecule delivery particle used to determine a quantitative ratio may be the same or different. In the case of different molecule delivery particles, the molecule delivery particle used to determine a quantitative ratio includes, for example, a coat comprising substantially the same composition as that of the molecule delivery particle used to determine an isosbestic point and a delivery molecule, and includes a first particle and a second particle at an unknown ratio.

The isosbestic point may be, for example, the wavelength at the intersection of a fitted curve of the molar extinction coefficients of the second particle at a plurality of measurement wavelengths and a fitted curve of the molar extinction coefficients of the first delivery molecule at a plurality of measurement wavelengths. In one example, by plotting the molar extinction coefficients of the second particle at a plurality of measurement wavelengths on a graph with the measurement wavelength on the horizontal axis and the molar extinction coefficient on the vertical axis, a scatter diagram is obtained, and a fitted curve for the second particle of the plot corresponding to each molar extinction coefficient in the scatter diagram is obtained. Similarly, a scatter diagram of the molar extinction coefficients of the first delivery molecule at a plurality of measurement wavelengths is obtained, and a fitted curve for the first delivery molecule of the plot corresponding to each molar extinction coefficient in the scatter diagram is obtained. The intersection of the fitted curve for the second particle and the fitted curve for the first delivery molecule is identified, and the wavelength at the intersection can be taken as the isosbestic point.

As the quantitative ratio between the first particle and the second particle, for example, when the first particle is a full virus particle including a capsid and genomic DNA and the second particle is an empty virus particle including a capsid but not including genomic DNA, the ratio between the number of the full virus particles and the number of the empty virus particles can be calculated by using the following numerical expression. The quantitative ratio obtained by the present method is characterized as not a relative concentration ratio but a ratio of the numbers of virus particles (absolute ratio).

$$\frac{[N_{empty}]}{[N_{full}]} = \frac{2 \times \text{Area}_{empty}}{\text{Area}_{empty} + \text{Area}_{DNA}} = \frac{2 \times \text{Area}_{empty}}{\text{Area}_{full}} \qquad \text{[Equation 4]}$$

where $N_{empty}$ and $N_{full}$ represent the particle numbers of the empty virus particles and the full virus particles, respectively, and $\text{Area}_{empty}$ and $\text{Area}_{full}$ ($=\text{Area}_{empty}+\text{Area}_{DNA}$) represent the area of a peak corresponding to the full virus particles and the area of a peak corresponding to the empty virus particles in the sedimentation coefficient distribution, respectively.

In the above example, the quantitative ratio between the first particle and the second particle was calculated by using a full virus particle as the first particle and an empty virus particle as the second particle, and the quantitative ratio between particles other than those can also be calculated. For example, when the molecule delivery particle is a liposome, the constant "2" shown in the numerator in the above numerical expression is appropriately changed based on the molecular weight of the coat and the molecular weight of the delivery molecule, and then on the assumption that a full liposome particle including a lipid bilayer as a coat and a drug encapsulated therein is the first particle and an empty liposome particle including a lipid bilayer but not including a drug is the second particle, the quantitative ratio between those particles can be calculated by using the changed numerical expression. For example, according to the "Method for characterizing molecule delivery particle including determining molecular weight" described above, the molecular weights of a full particle including a delivery molecule and a coat and an empty particle composed of a coat not including a delivery molecule are determined, and when the molecular weight of the delivery molecule included in the full particle corresponds to the molecular weight of one designed molecule or one desired molecule, "2" can be set, and when the molecular weight thereof corresponds to the molecular weight of two designed molecules or two desired molecules, "3" can be set.

(2) Method for Characterizing Molecule Delivery Particle Including Determining Quantitative Ratio at Isosbestic Point Once the isosbestic point is determined for a specific molecule delivery particle, for a molecule delivery particle including a coat comprising substantially the same composition as that of the specific molecule delivery particle and a delivery molecule, the quantitative ratio between the first particle and the second particle in the molecule delivery particle can be determined by particle separation with optical measurement at the isosbestic point, without using the molar extinction coefficient. The specific molecule delivery particle may be the same as or different from the molecule delivery particle used to determine an isosbestic point. In the case of different molecule delivery particles, the molecule delivery particle including a first particle and a second particle between which a quantitative ratio is determined includes, for example, a coat comprising substantially the same composition as that of the molecule delivery particle used to identify an isosbestic point and a delivery molecule, and includes the first particle and the second particle at an unknown ratio.

Therefore, one aspect of the present invention provides a method for characterizing a molecule delivery particle including determining a quantitative ratio, without using a molar extinction coefficient. Specifically, the method includes: subjecting a molecule delivery particle including a first particle and a second particle to particle separation with optical measurement at an isosbestic point to determine an absorbance of each of the first particle and the second particle; and determining a quantitative ratio between the first particle and the second particle by using the absorbance of each of the first particle and the second particle. To each step of the method, the description and embodiments given for the corresponding step of the method described above apply accordingly.

In one embodiment, the method for characterizing a molecule delivery particle including a first particle and a second particle includes: determining an absorbance of each of the first particle and the second particle from absorbance data of the molecule delivery particle obtained by particle separation with optical measurement at an isosbestic point; and determining a quantitative ratio between the first particle and the second particle by using the absorbance of each of the first particle and the second particle.

(3) Method for Characterizing Molecule Delivery Particle Including Determining Quantitative Ratio at Measurement Wavelength at which Molar Extinction Coefficient of Particle has been Determined Once the molar extinction coefficient is determined for a specific molecule delivery particle at a specific measurement wavelength, for a molecule delivery particle including a coat comprising substantially the same composition as that of the specific molecule delivery particle and a delivery molecule, the quantitative ratio between the first particle and the second particle can be determined by determining an absorbance of each of the first particle and the second particle in the molecule delivery particle by particle separation with optical measurement at the specific measurement wavelength. The specific molecule delivery particle may be the same as or different from the molecule delivery particle used to determine a molar extinction coefficient at a specific measurement wavelength. In the case of different molecule delivery particles, the specific molecule delivery particle includes a coat comprising substantially the same composition as that of the molecule delivery particle used to determine a molar extinction coefficient at a specific measurement wavelength and a delivery molecule, and includes a first particle and a second particle at an unknown ratio.

Therefore, one aspect of the present invention provides a method for characterizing a molecule delivery particle including determining a quantitative ratio at a measurement wavelength at which a molar extinction coefficient of the particle has been determined. Specifically, the method includes: subjecting a molecule delivery particle including a first particle and a second particle to particle separation with optical measurement at a measurement wavelength at which a molar extinction coefficient of each of the first particle and the second particle has been determined, to determine an absorbance of each of the first particle and the second particle; and determining a quantitative ratio between the first particle and the second particle by using the absorbance of each of the first particle and the second particle and the determined molar extinction coefficient of each of the first particle and the second particle. In determining the quantitative ratio in the present embodiment, for example, by dividing the peak area corresponding to the first particle in the sedimentation coefficient distribution for absorbance by the molar extinction coefficient of the first particle, the molar concentration of the first particle is obtained. From the molar concentration of the second particle obtained in the same manner and the molar concentration of the first particle, the quantitative ratio between the first particle and the second particle can be determined. In one embodiment, the first particle and the second particle whose molar extinction coefficients have been determined in advance and the first particle and the second particle whose quantitative ratio is determined each include a coat comprising substantially the same composition or the same composition and a delivery molecule.

In one embodiment, the method for characterizing a molecule delivery particle including a first particle and a second particle includes: determining an absorbance of each of the first particle and the second particle from absorbance data of the molecule delivery particle obtained by particle separation with optical measurement at a measurement wavelength at which a molar extinction coefficient of each of the first particle and the second particle has been determined; and determining a quantitative ratio between the first particle and the second particle by using the absorbance of each of the first particle and the second particle and the determined molar extinction coefficient of each of the first particle and the second particle.

In the above embodiment, a molecule delivery particle including a first particle and a second particle was given as an example, but the molecule delivery particle used in the present aspect is not limited thereto. The molecule delivery particle used in the present aspect may include three types of particles (for example, first particle, second particle, and third particle) or four or more types of particles.

The method described above can be used for quality control of the molecule delivery particle. In one example, the present method can be used to control the quality of a recombinant virus particle that is a molecule delivery particle for gene therapy. Specifically, the recombinant virus particle may include, in addition to a desired virus particle that includes a predetermined genome, an undesired virus particle that does not include the predetermined genome. By determining the ratio of the number of the desired virus particle or the undesired virus particle to the number of all virus particles by using the present method, the quality of the recombinant virus particle can be controlled.

Method for Characterizing Molecule Delivery Particle Including Determining the Degree of Contribution to Absorbance of Third Particle One aspect of the present invention provides a method for characterizing a molecule delivery particle including determining a degree of contribution to an absorbance of a third particle. In the method, a molecule delivery particle including a first particle, a second particle, and a third particle can be used. The third delivery molecule has a third coat and may or may not have a third delivery molecule. The method includes: determining, by particle separation with optical measurement at a plurality of measurement wavelengths of the molecule delivery particle, an absorbance of the third particle for each measurement wavelength of the measurement wavelengths; and determining a degree of contribution of the molar extinction coefficient of the second particle and the molar extinction coefficient of the first delivery molecule to the absorbance of the third particle. The particle separation with optical measurement to determine an absorbance of the third particle, the particle separation with optical measurement to determine an increment in refractive index, and the particle separation with optical measurement to determine an absorbance may be carried out simultaneously or sequentially. In one embodiment, the three particle separations with optical measurement are carried out simultaneously.

The first particle, the second particle, and the third particle include, for example, a first coat, a second coat, and a third coat comprising substantially the same composition, respectively. The coats comprising substantially the same composition may be, for example, proteinaceous (for example, capsid protein or albumin) coats, lipid bilayer coats, or polymer (for example, PEG or PLGA) coats. The coat of each particle may have, for example, substantially the same composition and have substantially the same size. As one example of the coat, when the molecule delivery particle is a virus particle, the coat is substantially the same proteinaceous capsid and has substantially the same size (for example, capsid monomer). As a further example of the coat, when the molecule delivery particle is a virus particle, the coat is the same proteinaceous capsid, two types of the three types of particles have a coat comprising the same size (for example, capsid monomer), and the remaining one type may have a coat comprising a different size (for example, aggregate). In the above example, a virus particle was given as an example of the molecule delivery particle, but the molecule delivery particle is not limited thereto. When the molecule delivery particle is a liposome, the coat thereof may be a lipid bilayer comprising the same composition and may have approximately the same size (for example, a particle size distribution represented by a single peak).

In one example, the first particle and the third particle may include, for example, a first delivery molecule and a third delivery molecule comprising substantially the same composition, respectively. The delivery molecule comprising substantially the same composition may be, for example, a polynucleotide, a polypeptide, an organic compound, or a radioactive substance, or a combination thereof. When the molecule delivery particle is a virus particle, the delivery molecule is a polynucleotide. In one example, the first particle includes a polynucleotide comprising a desired size, and the third particle may include a polynucleotide smaller than the desired size (for example, a fragment of a desired polynucleotide) or a polynucleotide larger than the desired size (for example, an aggregate of the desired polynucleotide). In the above example, a third delivery molecule comprising substantially the same composition as that of the first delivery molecule was given as an example, but the third delivery molecule used in the present aspect is not limited thereto. In one example, the third particle used in the present aspect may include a third delivery molecule comprising a composition different from that of the first delivery molecule (for example, a different type of molecule). In this example, the wavelength-dependent molar extinction coefficient of the third delivery molecule can be determined by a known method.

The absorbance of the third particle at each measurement wavelength can be determined, for example, according to the method described in the Examples or the description of the "step of determining an absorbance" in the "Method for characterizing molecule delivery particle including determining molar extinction coefficient" from optical data (including, for example, absorbance data) of a molecule delivery particle including a first particle, a second particle, and a third particle obtained by subjecting the molecule delivery particle to particle separation with optical measurement at a plurality of measurement wavelengths. Therefore, the method for characterizing a molecule delivery particle including determining a concentration of a third particle includes determining an absorbance of the third particle at each measurement wavelength from optical data (including, for example, absorbance data) of the molecule delivery particle.

The degree of contribution of the molar extinction coefficient of the second particle (comprising a second coat) and the molar extinction coefficient of the first component to the absorbance of the third particle (that can have a third coat and a third delivery molecule) can be determined according to the method described in the Examples. Specifically, the absorbance of the third particle is the total value of a value obtained by multiplying the molar extinction coefficient of the second particle (second coat) comprising the same composition as that of the third coat by the degree of contribution $\alpha$ plus a value obtained by multiplying the molar extinction coefficient of the third delivery molecule comprising the same composition as that of the third delivery molecule by the degree of contribution $\beta$, and thus the degrees of contribution $\alpha$ and $\beta$ can be determined by carrying out multiple regression analysis of the absorbance of the third particle at each measurement wavelength by using the molar extinction coefficient of the second particle and the molar extinction coefficient of the first delivery molecule at each measurement wavelength.

In one embodiment, the method for characterizing a molecule delivery particle including determining a degree of contribution to an absorbance of a third particle includes determining an absorbance of the third particle for each measurement wavelength from absorbance data; and determining a degree of contribution of a molar extinction coefficient of a second particle and a molar extinction coefficient of a first delivery molecule to the absorbance of the third particle.

In one embodiment, the method of characterizing a molecule delivery particle including determining a degree of contribution to an absorbance of a third particle may further include determining a proportion of the third delivery molecule based on the degrees of contribution ($\alpha$ and $\beta$). In one example, in a third particle (that may have a third coat and a third delivery molecule), the proportion of the third delivery molecule to the third coat comprising the same composition as that of the second coat (=$\beta/\alpha$) can be calculated. In a further example, in the third particle (that has a third coat and a third delivery molecule), the proportion of the third coat (=$\alpha/(\alpha+\beta)$) or the proportion of the third delivery molecule (=$\beta/(\alpha+\beta)$) can be calculated.

In one embodiment, the method of characterizing a molecule delivery particle including determining a degree of contribution to an absorbance of a third particle may further include determining a molar concentration of each of the third coat and the third delivery molecule based on the degrees of contribution. The concentration of each of the third coat and the third delivery molecule can be determined according to the method described in the Examples. Specifically, the concentration of the third coat in the third particle can be obtained by multiplying a molar extinction coefficient of the coat (empty particle) by the degree of contribution α thereof to obtain a peak area of the coat (absorbance of the coat) in a peak area of the third particle (absorbance of the third particle), dividing the obtained peak area of the coat by the molar extinction coefficient of the coat (empty particle), and converting an optical path length in optical measurement. Similarly, the concentration of the third delivery molecule in the third particle can be obtained by multiplying a molar extinction coefficient of the delivery molecule (delivery molecule included in the full particle) by the degree of contribution β thereof to obtain a peak area of the delivery molecule (absorbance of the delivery molecule) in a peak area of the third particle (absorbance of the third particle), dividing the obtained peak area of the delivery molecule by the molar extinction coefficient of the delivery molecule (delivery molecule included in the full particle), and converting an optical path length in optical measurement.

In one embodiment, the method for characterizing a molecule delivery particle including determining a degree of contribution to an absorbance of a third particle may further include determining a ratio of a content of the third delivery molecule to a content of the third coat (=[content of third delivery molecule]/[content of third coat]) in a peak corresponding to the third particle. The content of the third delivery molecule relative to the content of the third coat can be obtained by dividing the concentration of the third delivery molecule obtained according to the embodiment described above by the concentration of the third coat.

In one embodiment, the method for characterizing a molecule delivery particle including determining a degree of contribution to an absorbance of a third particle may further include, when the molecule delivery particle is a recombinant virus particle and the delivery molecule is a polynucleotide, determining a ratio of a length of a polynucleotide included in the third particle to a length of a polynucleotide included in the full particle (=[length of polynucleotide of third particle]/[length of polynucleotide of full particle]). The ratio of the length of the polynucleotide included in the third particle to the length of the polynucleotide included in the full particle can be calculated by using the degree of contribution β and a concentration of a capsid (empty particle) ($C_{capsid}$) in Equation 13 and Equation 14.

In the above embodiment, a molecule delivery particle including a first particle, a second particle, and a third particle was given as an example, but the molecule delivery particle used in the present aspect is not limited thereto. The molecule delivery particle used in the present aspect may include four types of particles (for example, first particle, second particle, third particle, and fourth particle) or five or more types of particles.

Method for Characterizing Molecule Delivery Particle Including Determining Quality One aspect of the present invention provides a method for characterizing a molecule delivery particle including determining quality. In one embodiment, the method includes determining that the molecule delivery particle has a predetermined quality based on a quantitative ratio between the first particle and the second particle. In the method, a molecule delivery particle including a first particle and a second particle wherein the first particle has a first coat and a first delivery molecule, and the second particle has a second coat can be used. The quantitative ratio between the first particle and the second particle can be determined according to the "Method for characterizing molecule delivery particle including determining quantitative ratio" described above.

The quality of the molecule delivery particle is determined by whether or not the quantitative ratio between the first particle and the second particle exceeds a predetermined threshold. The threshold is appropriately set according to a circumstance such as using the molecule delivery particle in the present aspect. In one example, it is determined that a molecule delivery particle including a first particle and a second particle has a predetermined quality when the quantitative ratio (preferably percentage) between the first particle and the second particle exceeds a threshold. The predetermined quality is appropriately set according to the use of the molecule delivery particle. As an expression of the determination described above, "have a predetermined quality" was given as an example, but the expression of the determination of the present case is not limited thereto. The determination may be, for example, "have a high quality."

In one example, if the molecule delivery particle is a recombinant virus particle for gene therapy, the first virus particle has a capsid, which is a first coat, and DNA comprising a desired size, which is a first delivery molecule, and the second virus particle has the capsid as a second coat and does not have DNA, when the percentage of the number of the desired first virus particle to the number of the recombinant virus particle including the first virus particle and the second virus particle exceeds a first threshold (for example, 95%), it is determined that the molecule delivery particle has a predetermined quality. In the above example, when the percentage of the number of the desired first virus particle to the number of the recombinant virus particle is equal to or less than the first threshold, it is determined that the molecule delivery particle does not satisfy the predetermined quality. In a further example, when the percentage of the number of the desired second virus particle to the number of the recombinant virus particle exceeds a first threshold (for example, 95%), it is determined that the molecule delivery particle has a predetermined quality. In the above example, when the percentage of the number of the desired second virus particle to the number of the recombinant virus particle is equal to or less than the first threshold, it is determined that the molecule delivery particle does not satisfy the predetermined quality.

In the above examples, the case of using one threshold (for example, a first threshold) was given as an example, but the number of thresholds used in the present embodiment is not limited to one. In one example, the threshold may include two thresholds (for example, a first threshold and a second threshold that is a higher value than the first threshold). In one example, when the proportion of the number of a desired second particle to the number of a molecule delivery particle including a first particle and the second particle exceeds a first threshold and is equal to or less than a second threshold, it is determined that the molecule delivery particle has a predetermined quality. In this example, when the above proportion exceeds the second threshold, it is determined that the molecule delivery particle has an excellent quality.

In one embodiment, the method for characterizing a molecule delivery particle including determining quality includes: determining, for a molecule delivery particle including a first particle, a second particle, and a third particle (comprising a third coat and a third delivery molecule), a quantitative ratio of the first particle or the second particle to the molecule delivery particle based on a molar concentration of the first particle, a molar concentration of the second particle, a concentration of the third coat, and a concentration of the third delivery molecule; and determining that the delivery particle has a predetermined quality when the quantitative ratio exceeds a first threshold. The molar concentration of the first particle and the molar concentration of the second particle can be determined according to the "Method for characterizing molecule delivery particle including determining molar concentration" described above. The concentration of the third coat and the concentration of the third delivery molecule can be determined based on the degree of contribution determined according to the "Method for characterizing molecule delivery particle including determining the degree of contribution to absorbance of third particle" described above. In one example, the concentration of the third coat and the concentration of the third delivery molecule can collectively be the concentration of the third particle. Therefore, the method for characterizing a molecule delivery particle including determining quality according to one embodiment includes determining, based on the molar concentration of a first particle, the molar concentration of a second particle, and the concentration of a third particle, a quantitative ratio of the first particle or the second particle to a molecule delivery particle including those three particles and determining that the molecule delivery particle has a predetermined quality when the quantitative ratio exceeds a first threshold. The descriptions of thresholds and determination expressions given for other embodiments of the present case are appropriately provided for the present embodiment.

In one example, if the molecule delivery particle is a recombinant virus particle for gene therapy, the first virus particle has a capsid, which is a first coat, and DNA of a desired size, which is a first delivery molecule, the second virus particle has the capsid as a second coat and does not have DNA, and the third particle has a capsid, which is a third coat, and DNA (for example, a DNA fragment of a desired size or an aggregate of the DNA) as a third delivery molecule, when the percentage of the number of the desired first virus particle to the number of a recombinant virus particle including the first virus particle, the second virus particle, and the third virus particle exceeds a first threshold (for example, 95%), it is determined that the molecule delivery particle has a predetermined quality. In the above example, when the percentage of the number of the undesired second virus particle to the number of the recombinant virus particle is equal to or less than a second threshold (for example, 5%) that is a smaller value than the first threshold, it is determined that the molecule delivery particle has an excellent quality. In a further example, when the percentage of the total number of the undesired second virus particle and third virus particle to the number of the recombinant virus particle is equal to or less than a third threshold (for example, 3%) that is a smaller value than the first threshold, it is determined that the molecule delivery particle has an excellent quality. In the above example, when the percentage of the number of the desired first virus particle to the number of the recombinant virus particle is equal to or less than the first threshold and equal to or more than the third threshold, it is determined that the molecule delivery particle does not satisfy the predetermined quality.

In the above embodiment, a molecule delivery particle including a first particle and a second particle, or a molecule delivery particle further including a third particle was given as an example, but the molecule delivery particle used in the present aspect is not limited thereto. The molecule delivery particle used in the present aspect may include four types of particles (for example, first particle, second particle, third particle, and fourth particle) or five or more types of particles.

Method for Characterizing Molecule Delivery Particle Including Determining Absorbance Ratio One aspect of the present invention provides a method for characterizing a molecule delivery particle including determining an absorbance ratio. The method includes: subjecting a molecule delivery particle to particle separation with optical measurement at a first measurement wavelength and a second measurement wavelength to determine an absorbance of the molecule delivery particle for each of the first measurement wavelength and the second measurement wavelength; and determining an absorbance ratio from the absorbance of the molecule delivery particle at the first measurement wavelength and the absorbance of the molecule delivery particle at the second measurement wavelength.

The "step of determining an absorbance" in the above method can be carried out in the same manner as the "step of determining an absorbance" in the "Method for characterizing molecule delivery particle including determining molar extinction coefficient" described above. Specifically, by subjecting a molecule delivery particle to particle separation with optical measurement at a first measurement wavelength and a second measurement wavelength, optical data (including, for example, absorbance data) of the molecule delivery particle is obtained. The optical data includes information about the absorbance of the molecule delivery particle for each of the first measurement wavelength and the second measurement wavelength. From the optical data, the absorbance of the molecule delivery particle is determined for each of the first measurement wavelength and the second measurement wavelength according to the method described in the Examples or the description of the "step of determining an absorbance" in the "Method for characterizing molecule delivery particle including determining molar extinction coefficient." For example, the absorbance ratio can be calculated by dividing the determined absorbance of the molecule delivery particle at the first measurement wavelength by the determined absorbance of the molecule delivery particle at the second measurement wavelength.

In one example, when the molecule delivery particle is a recombinant virus particle and includes a full virus particle as the first particle and an empty virus particle as the second particle, the method includes: subjecting the molecule delivery particle to particle separation with optical measurement at 260 nm and 280 nm to determine respective absorbances of the full virus particle and the empty virus particle for each of 260 nm and 280 nm; and determining an absorbance ratio ($=A260/A280$) of each of the full virus particle and the empty virus particle by dividing the respective absorbances of the full virus particle and the empty virus particle at the 260 nm (A260) by the respective absorbances of the full virus particle and the empty virus particle at 280 nm (A280). The absorbance ratios obtained in this example indicate the purity of each of the first particle and the second particle included in the molecule delivery particle. Therefore, the method for characterizing a molecule delivery particle including determining an absorbance ratio can be used as a method for determining a purity of a molecule delivery particle. In the above example, a recombinant virus particle was given as an example of the molecule delivery particle, but the molecule delivery particle that can be used in the method is not limited thereto. The molecule delivery particle may be, for example, a liposome, an albumin particle, a micelle, or a PLGA particle. The measurement wavelength used in the method is appropriately set by those skilled in the art in consideration of the absorption maximum of the coat or the molecule to be delivered as a subject to be measured.

In one embodiment, the method for characterizing a molecule delivery particle including determining an absorbance ratio includes: determining, from optical data (including absorbance data) of the molecule delivery particle obtained by centrifugation with optical measurement, an absorbance of the molecule delivery particle for each of the first measurement wavelength and the second measurement wavelength; and determining an absorbance ratio from the absorbance at the first measurement wavelength and the absorbance at the second measurement wavelength.

In one embodiment, the method for characterizing a molecule delivery particle includes: determining, from absorbance data of the molecule delivery particle obtained by particle separation with optical measurement at a first measurement wavelength and a second measurement wavelength, an absorbance of the molecule delivery particle for each of the first measurement wavelength and the second measurement wavelength; and determining an absorbance ratio from the absorbance at the first measurement wavelength and the absorbance at the second measurement wavelength.

Method for Determining Molar Extinction Coefficient of First Particle

One aspect of the present invention provides a method for determining a molar extinction coefficient of a first particle. In the method, the first particle includes a first coat and a first polynucleotide of a first chain length. The method includes: calculating an average molar extinction coefficient per nucleotide by dividing a molar extinction coefficient of a second polynucleotide by a value corresponding to a chain length thereof; and determining a molar extinction coefficient of the first particle by adding a molar extinction coefficient of the first coat and the molar extinction coefficient of the first polynucleotide. When the second polynucleotide is 500 nucleotides in length, the value corresponding to that chain length is "500." The method includes: calculating an average molar extinction coefficient per nucleotide by dividing a molar extinction coefficient of a second polynucleotide of a predetermined chain length by a value of the predetermined chain length; and determining a molar extinction coefficient of the first particle by adding a molar extinction coefficient of the first coat and the molar extinction coefficient of the first polynucleotide.

The second polynucleotide used in the present aspect is designed to have a predetermined chain length. The second polynucleotide can be prepared, for example, by using a known polynucleotide synthesis method, PCR, or genetic engineering technique, or a combination thereof. The first polynucleotide used in the present aspect is designed to have a first chain length. The first chain length may be the same as or different from the predetermined chain length of the second polynucleotide. In one embodiment, the first chain length is different from the predetermined chain length of the second polynucleotide. The first polynucleotide and the second polynucleotide may each be a DNA molecule or an RNA molecule. The DNA molecule or the RNA molecule may be single-stranded or double-stranded. The chain lengths of the first polynucleotide and the second polynucleotide are not particularly limited. In one example, the first polynucleotide and the second polynucleotide may each be a polynucleotide that is 500 to 10,000 nucleotides in length, 1,000 to 8,000 nucleotides in length, or 2,000 to 6,000 nucleotides in length.

The molar extinction coefficient of the second polynucleotide can be determined, for example, by the "Method for characterizing molecule delivery particle including determining molar extinction coefficient of first delivery molecule." In one example, the molar extinction coefficient of the second polynucleotide can be determined by carrying out the "Method for characterizing molecule delivery particle including determining molar extinction coefficient of first delivery molecule" on a molecule delivery particle including a second particle including a second coat comprising substantially the same composition and substantially the same size as that of the first coat and a second polynucleotide, and a third particle including a third coat comprising substantially the same composition and substantially the same size as that of the first coat. In this step, the molar extinction coefficient of the second coat is also determined. The average molar extinction coefficient per nucleotide can be calculated by dividing the extinction coefficient of the second polynucleotide thus determined by a value corresponding to the chain length thereof. The molar extinction coefficient of the first polynucleotide can be calculated by multiplying the calculated average molar extinction per nucleotide by the value of the first chain length. When either one of the first polynucleotide and the second polynucleotide is a single-stranded polynucleotide and the other is a double-stranded polynucleotide, the value obtained by doubling the molar extinction coefficient of the single-stranded polynucleotide and multiplying the doubled molar extinction coefficient by 0.9 can be used as the molar extinction coefficient of the double-stranded polynucleotide. This is because a hypochromic effect reduces the molar extinction coefficient of a double-stranded DNA molecule by about 10% from the total value of the molar extinction coefficient of each of the two single-stranded DNA molecules constituting the double-stranded DNA molecule.

The second coat, whose molar extinction coefficient has been determined by the "Method for characterizing molecule delivery particle including determining molar extinction coefficient of first delivery molecule" described above, has substantially the same composition and substantially the same size as that of the first coat, and thus the molar extinction coefficient of the second coat can be the molar extinction coefficient of the first coat. By adding the molar extinction coefficient of the first coat and the molar extinction coefficient of the first polynucleotide thus calculated, the molar extinction coefficient of the first particle can be determined.

In one example, the second particle may be a recombinant virus particle including a designed genomic DNA molecule and a capsid, and the first particle may be a recombinant virus particle including a DNA molecule designed for gene therapy and having a different chain length from that of the genomic DNA molecule and the capsid. In the above example, recombinant virus particles were given as examples, but the particles used in the aspect are not limited thereto. In one example, the second particle may be a liposome including a designed DNA molecule and a lipid bilayer, and the first particle may be a liposome including a DNA molecule designed for gene therapy and having a different chain length from that of the designed DNA molecule and a lipid bilayer.

Method for Determining Molar Extinction Coefficient of Polynucleotide of Predetermined Chain Length One aspect of the present invention provides a method for determining a molar extinction coefficient of a polynucleotide of a predetermined chain length. The method includes, when measuring a molecule delivery particle including the polynucleotide at a predetermined measurement wavelength, multiplying an average molar extinction coefficient per nucleotide at any one wavelength listed in the following table that is the same as or corresponds to the predetermined measurement wavelength by a value of the predetermined chain length to determine a molar extinction coefficient of the polynucleotide at the any one wavelength.

TABLE 1

| TABLE | |
| Wavelength (nm) | Average molar extinction coefficient per nucleotide $[\times 10^7 \text{ L mol}^{-1} \text{ cm}^{-1}]$ |
| --- | --- |
| 230 | $4.391 \times 10^{-4}$ |
| 235 | $4.849 \times 10^{-4}$ |
| 240 | $5.463 \times 10^{-4}$ |
| 245 | $6.339 \times 10^{-4}$ |
| 250 | $7.488 \times 10^{-4}$ |
| 255 | $8.336 \times 10^{-4}$ |
| 260 | $8.648 \times 10^{-4}$ |
| 265 | $8.058 \times 10^{-4}$ |
| 270 | $7.256 \times 10^{-4}$ |
| 275 | $6.255 \times 10^{-4}$ |
| 280 | $5.060 \times 10^{-4}$ |

The method for determining a molar extinction coefficient of a polynucleotide of a predetermined chain length can be used, for example, when the quality of a molecule delivery particle including the polynucleotide is determined by measuring the absorbance of the molecule delivery particle at a predetermined measurement wavelength, as in the "Method for characterizing molecule delivery particle including determining quality." The term "predetermined measurement wavelength" according to the present aspect is any one wavelength between 220 and 320 nm. In one example, the predetermined measurement wavelength may be any one wavelength between, for example, 220 and 310 nm, 220 and 300 nm, or 220 and 290 nm. As used herein, the term "wavelength corresponding to a predetermined measurement wavelength" means the wavelength shown in the table that is closest to the predetermined measurement wavelength. When two wavelengths are closest to the predetermined measurement wavelength, the wavelength corresponding to the predetermined measurement wavelength is the shorter wavelength of the two wavelengths. In one example, when the predetermined measurement wavelength is any one wavelength between 220 and 232.5 nm, the wavelength corresponding to the predetermined measurement wavelength is 230 nm, the wavelength shown in the table closest to the predetermined measurement wavelength. In one example, when the predetermined measurement wavelength is 232.5 nm, the two wavelengths shown in the table closest to the predetermined measurement wavelength are 230 nm and 235 nm. In the above example, the wavelength corresponding to the predetermined measurement wavelength (i.e., 232.5 nm) is 230 nm, which is the shorter wavelength of the two wavelengths.

In one example, the molar extinction coefficient at a wavelength of 280 nm of a polynucleotide that is 1,000 nucleotides in length is $5.06 \times 10^{-1} [\times 10^7 \text{ L mol}^{-1} \text{ cm}^{-1}]$, which is the value obtained by multiplying $5.06 \times 10^{-4} [\times 10^7 \text{ L mol}^{-1} \text{ cm}^{-1}]$ by a chain length value of 1,000.

The molar extinction coefficient per nucleotide at each wavelength shown in the above table is a value obtained from the molar extinction coefficient of single-stranded DNA of a predetermined chain length. In one example, when the polynucleotide of a predetermined chain length is double-stranded DNA, the molar extinction coefficient of a double-stranded DNA molecule of the predetermined chain length is the value obtained by doubling the value obtained by multiplying the average molar extinction coefficient per nucleotide shown in the above table by the value of the predetermined chain length and multiplying the doubled value by 0.9. In one example, when the polynucleotide of a predetermined chain length is single-stranded RNA, the molar extinction coefficient of a single-stranded RNA molecule of the predetermined chain length is the value obtained by multiplying the average molar extinction coefficient per nucleotide shown in the above table by the value of the predetermined chain length. This is because the average molar extinction coefficient of DNA and the average molar extinction coefficient of RNA are approximately equal to each other.

Unless otherwise specified, the descriptions of the terms and the embodiments provided by the present disclosure are appropriately applied among the aspects and embodiments provided by the present disclosure.

Hereinafter, specific Examples will be described, but these represent preferable embodiments of the present invention and do not limit the invention defined in the attached claims in any way.

EXAMPLES

Materials and Methods

Samples

An adeno-associated virus serotype 5 (AAV5) vector including a complete vector genome (full particle, AAV5-FP) and an AAV5 vector not including the vector genome (empty particle, AAV5-EP) were provided by the Manufacturing Technology Association of Biologics (Tokyo). As 180 water ($H_2^{18}O$), one concentrated to 98% was purchased from Taiyo Nippon Sanso Corporation (Tokyo). A stock solution of PBS ($\times 10$) was purchased from Thermo Scientific (USA). Poloxamer 188 (European Pharmacopoeia reference material) was purchased from Sigma-Aldrich, Inc. (USA). The other reagents were purchased from FUJIFILM Wako Pure Chemical Corporation (Osaka).

Sample Preparation

For density contrast sedimentation velocity analytical ultracentrifugation (SV-AUC) experiments, finally AAV5-EP was concentrated to an absorbance at an optical path length of 1 cm of 0.95 at 280 nm and AAV5-FP was concentrated to an absorbance at an optical path length of 1 cm of 0.75 at 260 nm, by using Amicon Ultra 0.5 equipped with a 30 kDa filter membrane (Merck Millipore, US). The concentrated samples were diluted with a solvent or a solvent including $H_2^{18}O$ to prepare sample solutions including 0, 32.5, and 65% $H_2^{18}O$ of an absorbance of about 0.3 at an optical path length of 1.2 cm, respectively. For other SV-AUC experiments, each AAV stock solution was concentrated or diluted to prepare a test solution of an absorbance of about 0.3 at an optical path length of 1.2 cm.

UV Spectrum Measurement

UV measurement was carried out using a UV-1900 UV-VIS spectrophotometer (manufactured by Shimadzu Corporation).

Calculations

Calculation of Molecular Weight

The molecular weight of AAV-EP was calculated by using the program SEDNTERP (Laue, M. T. Computer-aided interpretation of analytical sedimentation data for proteins. Anal Ultracentrifugation Biochem Polym Sci 1992; 90-125). Specifically, the molecular weight of each structural protein was calculated from the amino acid compositions of VP1, VP2, and VP3, which are three structural proteins constituting the capsid of AAV. The molecular weight of AAV-EP was calculated on the assumption that AAV-EP included the structural proteins VP1:VP2:VP3 at a proportion of 5:5:50. The molecular weight of ssDNA was calculated at 801507.6 Da based on the designed DNA sequence.

Calculation of Partial Specific Volume

The partial specific volume of AAV-EP was calculated from the amino acid compositions thereof by using the program SEDNTERP (Laue, M. T. Computer-aided interpretation of analytical sedimentation data for proteins. Anal Ultracentrifugation Biochem Polym Sci 1992; 90-125). The partial specific volume of AAV-FP was calculated by using the following equation.

$$vbar_{AAV-FP} = \frac{vbar_{AAV-EP} \times Mw_{AAV-EP} + vbar_{ssDNA} \times Mw_{ssDNA}}{Mw_{AAV-EP} + Mw_{ssDNA}} \quad \text{Equation 1}$$

where $vbar_{AAV-FP}$, $vbar_{AAV-EP}$, and $vbar_{ssDNA}$ are the partial specific volumes (cm$^3$ g$^{-1}$) of AAV-FP, AAV-EP, and ssDNA, respectively. $Mw_{AAV-FP}$, $Mw_{AAV-EP}$, and $Mw_{ssDNA}$ are the partial specific volumes (cm$^3$ g$^{-1}$) of AAV-FP, AAV-EP, and ssDNA, respectively. As $vbar_{ssDNA}$, 0.54 cm$^3$ g$^{-1}$ reported in a previous study (Durchschlag H. Determination of the partial specific volume of conjugated proteins. Colloid Polym Sci 1989; 267:1139-1150) was used.

Calculation of Specific Refractive Index Increment (Dn/Dc)

The specific refractive index increment of AAV-EP was calculated from the amino acid compositions by using the SEDFIT (Schuck P. Sedimentation analysis of noninteracting and self-associating solutes using numerical solutions to the Lamm equation. Biophys J 1998; 75:1503-1512) program. The dn/dc of AAV-FP was calculated by using the following equation.

$$dn/dc_{AAV-FP} =$$
$$\frac{dn/dc_{AAV-EP} \times Mw_{AAV-EP} + dn/dc_{ssDNA} \times Mw_{ssDNA}}{Mw_{AAV-EP} + Mw_{ssDNA}} \quad \text{Equation 2}$$

where $dn/dc_{AAV-FP}$, $dn/dc_{AAV-EP}$, and $dn/dc_{ssDNA}$ are the specific refractive index increments (mL g-1) of AAV-FP, AAV-EP, and ssDNA, respectively. The dn/dc of ssDNA was 0.21 mL g$^{-1}$ as reported in a previous study (Davis T M, Wilson W D. Determination of the increments in refractive index of small molecules for correction of surface plasmon resonance data. Anal Biochem 2000; 284:348-353).

Calculation of Diffusion Coefficient, Friction Coefficient, and Stokes Radius

The diffusion coefficients of AAV-FP and AAV-EP were calculated using Svedberg's equation.

$$\frac{s}{D} = \frac{M(1 - vbar\rho_0)}{RT} \quad \text{Equation 3}$$

where s is the sedimentation coefficient (S), D is the diffusion coefficient (cm$^2$ sec$^{-1}$), M is the molecular weight (g mol$^{-1}$), vbar is (cm$^3$/g), $\rho_0$ is the solvent density (g mL$^{-1}$), R is the gas constant (8.314 J K$^{-1}$), and T is the absolute temperature (K). The Stokes radii of AAV-FP and AAV-EP were calculated using Stokes-Einstein's equation.

$$D = \frac{k_B T}{6\pi\eta_0 R_s} \quad \text{Equation 4}$$

where D is the diffusion coefficient (cm$^2$/sec), $k_B$ is the Boltzmann constant (1.38×10$^{-23}$ J/K), T is the absolute temperature (K), $\eta_0$ is the solvent viscosity, and $R_s$ is the Stokes radius (m). The friction coefficients of AAV-FP and AAV-EP were calculated using the following equation.

$$f = \frac{RT}{N_A D} \quad \text{Equation 5}$$

where D is the diffusion coefficient (cm$^2$/sec), R is the gas constant (8.314 J/K), T is the absolute temperature (K), $N_A$ is Avogadro's number (6.02×10$^{23}$ mol$^{-1}$), and f is the friction coefficient (g sec$^{-1}$).

Calculation of Sedimentation Coefficient, Radius of Gyration, Friction Ratio

The sedimentation coefficient and the radius of AAV5-EP were determined from the atomic coordinates of AAV5 (PDB code: 3ntt) by using the HYDROPRO (Ortega A, Amoros D, Garcia De La Torre J. Prediction of hydrodynamic and other solution properties of rigid proteins from atomic- and residue-level models. Biophys J 2011; 101:892-898) program.

Sedimentation Velocity Analytical Ultracentrifugation (SV-AUC)

SV-AUC experiments were carried out using AAV5-FP and AAV5-EP dissolved in a solvent (0.001 w/v % poloxamer 188 in PBS (pH 7.4)) or solvents including various concentrations of H$_2$$^{18}$O. The sample sectors of measurement cells equipped with a sapphire window and a 12 mm double sector centerpiece were each filled with 390 μL of a sample and the reference sector of each measurement cell was filled with 400 μL of a solvent. The optical path lengths of the sample sectors and the reference sectors are each 1.2 cm. The measurement cells were set in an analytical ultracentrifuge OPTIMA (Beckman Coulter, Inc., USA) and subjected to SV-AUC at a temperature of 20° C. and 10,000 rpm.

For UV detection, the measurement wavelength was set every 5 nm in the range of 230 nm to 280 nm for the samples not including H$_2$$^{18}$O. For the samples including H$_2$$^{18}$O, detection was carried out at 230 nm for both AAV-FP and AAV-EP. Data was acquired at radial increments of 10 μm without delay. The time-dependent sedimentation behavior in the measurement cells during centrifugation was obtained by measurement with an ultraviolet (UV) detection system and an interference (IF) detection system scanning the same measurement cell by using a multi-wavelength at intervals of 3 minutes and at intervals of 2 minutes, respectively. SV-AUC using a multi-wavelength detection system is also referred to as MW-SA-AUC. Absorbance data and refractive index data are obtained by measurement with a UV detection system and an IF detection system, respectively.

Data Analysis of SV-AUC

The data acquired by SV-AUC was analyzed by using the c(s) distribution model of the program SEDFIT (version 16.2b) (Schuck P. Sedimentation analysis of noninteracting and self-associating solutes using numerical solutions to the Lamm equation. Biophys J 1998; 75:1503-1512), fitting the friction ratio, the meniscus, the time-independent noise, and the radius-independent noise, and using a regularization level of 0.68. The evaluation was carried out with the sedimentation coefficient range set to 0 to 250 S and at a resolution of 500. The density and the viscosity of phosphate-buffered saline (PBS) were 1.00500 g mL$^{-1}$ and 1.0171 cP, respectively.

The densities and viscosities of buffers including 32.5% and 65% H$_2^{18}$O, respectively, were calculated by using the following equations obtained from the values disclosed in the literature (Brown P H, Balbo A, Zhao H, et al. Density Contrast Sedimentation Velocity for the Determination of Protein Partial-Specific Volumes. 6. Epub ahead of print 2011. DOI: 10.1371/journal.pone.0026221).

$$\rho = 0.001079 \times F_{H_2^{18}O} + \rho_0 \qquad \text{Equation 6}$$

$$\eta = 0.000495 \times F_{H_2^{18}O} + \eta_0 \qquad \text{Equation 7}$$

where FH$_2^{18}$O is the fraction of H$_2^{18}$O, $\rho_0$ is the density of PBS (g mL$^{-1}$), and $\eta_0$ is the viscosity of PBS (cP). The partial specific volume of the sample was set to 0.68 cm$^3$/g as an initial value. To estimate the partial specific volume, the sedimentation profiles of AAV5-EP or AAV5-FP in solutions of various densities were globally fit by using the "Hybrid Global Discrete Species Global Continuous Distribution" model of SEDPHAT as described by Brown et al. (Brown P H, Balbo A, Zhao H, et al. Density Contrast Sedimentation Velocity for the Determination of Protein Partial-Specific Volumes. 6. Epub ahead of print 2011. DOI: 10.1371/journal.pone.0026221). By using the obtained partial specific volume, the sedimentation coefficient distribution was defined. Then, the molecular weight was calculated from the sedimentation coefficient and the friction coefficient ratio (f/f$_0$) of each component. Charts of the c(s) distribution were prepared by using the program GUSSI (Brautigam C A. Calculations and Publication-Quality Illustrations for Analytical Ultracentrifugation Data. 1st ed. Elsevier Inc. Epub ahead of print 2015. DOI: 10.1016/bs.mie.2015.05.001.). The sedimentation coefficients obtained in the present study were reported as values normalized to standard conditions (s$_{20,w}$)

Characterization of Wavelength Versus Peak Area Plots of AAV-FP and AAV-EP

The peak areas at each measurement wavelength, As($\lambda$), of AAV-FP and AAV-EP were determined by integrating the main peaks in the C(s) distributions of AAV-FP and AAV-EP samples, respectively.

Determination of Molar Extinction Coefficient

The molar extinction coefficients of AAV5-FP, AAV5-EP, and the other AAV5-FP at each wavelength were determined using the following equation.

$$\varepsilon = \frac{As(\lambda) \times dn/dc \times Mw}{\Delta J \times \lambda_{IF}} \qquad \text{Equation 8}$$

where $\varepsilon$ represents the molar extinction coefficient (L mol$^{-1}$ cm$^{-1}$), dn/dc represents the specific refractive index increment (mL g$^{-1}$), Mw represents the molecular weight (kg mol$^{-1}$), $\Delta J$ represents the fringe displacement, and $\lambda_{IF}$ represents the wavelength (cm) of an interference signal. The molar extinction coefficient of ssDNA at each wavelength was estimated by subtracting the value of AAV5-EP from the value of AAV5-FP. In the present Example, the DNA sequence encapsulated in the capsid was designed to be common to the other AAV serotypes, and thus, the molar extinction coefficient of AAV-EP of the other serotypes at each wavelength was calculated by subtracting the value of ssDNA from the value of AAV-FP.

The molar extinction coefficient of ssDNA at each measurement wavelength thus obtained is summarized in the following table.

TABLE 2

| Wavelength | Molar extinction coefficient* ($\times 10^7$ L mol$^{-1}$ cm$^{-1}$) | | | | | |
|---|---|---|---|---|---|---|
| (nm) | AAV1-FP | AAV2-FP | AAV5-FP | AAV6-FP | AAV5-EP | ssDNA** |
| 230 | 5.448 | 5.961 | 5.565 | 5.601 | 4.424 | 1.141 (4.391 × 10$^{-4}$) |
| 235 | 3.430 | 3.662 | 3.591 | 3.486 | 2.331 | 1.260 (4.849 × 10$^{-4}$) |
| 240 | 2.316 | 2.399 | 2.363 | 2.339 | 0.943 | 1.420 (5.463 × 10$^{-4}$) |
| 245 | 2.133 | 2.234 | 2.134 | 2.172 | 0.486 | 1.648 (6.339 × 10$^{-4}$) |
| 250 | 2.313 | 2.406 | 2.309 | 2.329 | 0.363 | 1.946 (7.488 × 10$^{-4}$) |
| 255 | 2.575 | 2.692 | 2.552 | 2.603 | 0.386 | 2.167 (8.336 × 10$^{-4}$) |
| 260 | 2.656 | 2.801 | 2.721 | 2.693 | 0.473 | 2.248 (8.648 × 10$^{-4}$) |
| 265 | 2.674 | 2.815 | 2.671 | 2.712 | 0.577 | 2.094 (8.058 × 10$^{-4}$) |
| 270 | 2.552 | 2.698 | 2.582 | 2.601 | 0.696 | 1.886 (7.256 × 10$^{-4}$) |
| 275 | 2.355 | 2.515 | 2.407 | 2.404 | 0.781 | 1.626 (6.255 × 10$^{-4}$) |
| 280 | 2.082 | 2.195 | 2.138 | 2.109 | 0.822 | 1.315 (5.060 × 10$^{-4}$) |

*Obtained from SV-AUC analyses except for ssDNA
**Obtained by the subtracting of the value of AAV5-EP from that of AAV5-FP. The values in parentheses are the average molar extinction coefficient per nucleotide.

The chain length of ssDNA used in the present Example was 2599 nucleotides. The average molar extinction coefficient per nucleotide was calculated by dividing the molar extinction coefficient of ssDNA at each measurement wavelength by a value of the ssDNA chain length of 2,599. The average molar extinction coefficient per nucleotide for each measurement wavelength is shown in brackets in the rightmost column of the above table. The molar extinction coefficient of a polynucleotide of a predetermined chain length can be calculated using the average molar extinction coefficient per nucleotide obtained here.

Identification of Intermediate Particle/Aggregate by SV-AUC

In the identification of an intermediate particle observed in the region between the peaks of a full particle and an empty particle in the sedimentation coefficient distribution, or an aggregate observed in the region where the sedimentation coefficient was larger than that of a full particle, multiple regression analysis was carried out by using the plots of the molar extinction coefficients of each AAV-FP and ssDNA for 11 measurement wavelengths to determine the coefficients ($\alpha$ and $\beta$) described later.

$$A_{obs}(\lambda) = \text{Area}_{capsid}(\lambda) + \text{Area}_{ssDNA}(\lambda) \qquad \text{Equation 9}$$

$$\text{Area}_{capsid}(\lambda) = \alpha \times \varepsilon_{capsid}(\lambda) \qquad \text{Equation 10}$$

$$\text{Area}_{ssDNA}(\lambda) = \beta \times \varepsilon_{ssDNA}(\lambda) \qquad \text{Equation 11}$$

where $A_{obs}$ represents the area of the peak corresponding to the observed intermediate particle or aggregate; $\text{Area}_{capsid}$ and $\text{Area}_{ssDNA}$ represent the peak areas of the capsid of a virus particle (=AAV-EP) and ssDNA calculated based on equation 10 and equation 11, respectively; and $\varepsilon_{capsid}$ and $\varepsilon_{ssDNA}$ represent the molar extinction coefficients (L $\text{mol}^{-1}\text{cm}^{-1}$) of the capsid of a full virus particle (=AAV-EP) and ssDNA, respectively. Here, when the concentration of the capsid is $C_{capsid}$ and the numbers of a capsid and ssDNA in an unknown particle are $n_{capsid}$ and $n_{ssDNA}$, respectively, $\alpha$ and $\beta$ are as follows.

$$\alpha = C_{capsid} \times n_{capsid} \qquad \text{Equation 12}$$

$$\beta = C_{capsid} \times n_{ssDNA} \qquad \text{Equation 13}$$

In the case of a full particle, both $n_{capsid}$ and $n_{ssDNA}$ are 1, and in the case of an intermediate particle in which one capsid contains ssDNA of a chain length that is half the full length, $n_{capsid}$ is 1, and $n_{ssDNA}$ is 0.5. In addition, in the case of an aggregate in which two full particles are associated, $n_{capsid}$ is 2, and $n_{ssDNA}$ is 2, and in the case of an aggregate in which one full particle and one empty particle are associated, $n_{capsid}$ is 2, and $n_{ssDNA}$ is 1.

The chain length of a nucleotide encapsulated in an intermediate particle or an aggregate is calculated using the following equation.

$$N_{nucleotide} = N_{AAV-FP} \times \frac{n_{ssDNA}}{n_{capsid}} \qquad \text{Equation 14}$$

where $N_{nucleotide}$ represents the chain length of a nucleotide encapsulated in an intermediate particle or an aggregate, and $N_{AAV-FP}$ represents the chain length of a nucleotide encapsulated in a full particle.

Selection of Optimal Measurement Wavelength in SV-AUC Experiments

To evaluate the possibility of minimizing and optimizing the number of measurement wavelengths for determining the coefficients ($\alpha$ and $\beta$) expressed in equation 9, both coefficients were calculated by using data obtained from detection at two wavelengths and compared with those obtained by using data obtained from detection at 11 wavelengths. Further, multiple regression analysis was carried out using data derived from detection at three selected wavelengths (230 nm, 260 nm, and 280 nm).

Results

Characterization of Components in AAV Samples

To determine the partial specific volumes of AAV-5-EP and AAV5-FP, SV-AUC experiments were carried out using buffers comprising different densities resulting from varying concentrations of $H_2O$ and $H_2{}^{18}O$ (1.1 and 1.2 in FIG. 12). For AAV5-EP, the partial specific volume resulting from a global fit to the main component using SEDPHAT was 0.722 $\text{cm}^3\ \text{g}^{-1}$. As expected, this value is reasonably consistent with the calculated value (0.718 $\text{cm}^3\ \text{g}^{-1}$). The sedimentation coefficient distribution is shown in FIG. 1(A). The molecular weight of the main component (67.3 S) calculated using $f/f_0$, the solvent density, and the solvent viscosity was 3695.9 kDa, which is reasonably consistent with the calculated value (3705.5 kDa). For AAV5-FP, the partial specific volume resulting from a global fit using SEDPHAT to the main component was 0.686 $\text{cm}^3\ \text{g}^{-1}$, which was reasonably consistent with the calculated value (0.687 $\text{cm}^3\ \text{g}^{-1}$). The molecular weight of the main component (93.7 S) was calculated by using $f/f_0$, the solvent density, the solvent viscosity, and the partial specific volume and found to be 4914.2 kDa, which corresponds to the calculated value of the molecular weight of FP (4507.0 kDa) within the typical margin of error for the molecular weight from SV-AUC. The obtained parameters are summarized in FIG. 1(B). The above results concluded that the components of 67.3 S and 93.7 S are the empty particle and the full particle of AAV5, respectively.

Comparison Between Experimental Values of Partial Specific Volume and $f/f_0$ and Calculated Values Thereof from Three-Dimensional Coordinates From the s values, the molecular weights, and the partial specific volumes experimentally determined from SV-AUC, the D value of AAV5-EP was estimated at $1.54 \times 10^{-7}\ \text{cm}^2\ \text{sec}^{-1}$, and the D value of AAV5-FP was estimated at $1.46 \times 10^{-7}\ \text{cm}^2\ \text{sec}^{-1}$, by using Svedberg's equation (equation 3). As a result, the f value was calculated at $2.62 \times 10^{-7}\ \text{g}\ \text{sec}^{-1}$ for AAV-EP and $2.78 \times 10^{-7}\ \text{g}\ \text{sec}^{-1}$ for AAV5-FP, and the Stokes radius was 13.7 nm for AAV5-EP and 14.5 nm for AAV5-FP. Considering the deviation from SV-AUC, it is concluded that the difference is unimportant. The similarity in hydrodynamic behavior between AAV5-EP and AAV5-FP was consistent with the observation results by dynamic light scattering, and it was found that the Stokes radii of AAV5-EP and AAV5-FP were similar to each other. In addition, the f values of AAV5-EP and AAV5-FP were consistent with each other. Thus, it was suggested that AAV5-EP also generated friction with a water molecule during translational diffusion in a solution, as did AAV5-FP.

Hydrodynamic parameters can now be calculated from the three-dimensional coordinates of a protein, a protein complex, and a virus particle by the recent development of biophysical software (Ortega A, Amoros D, Garcia De La Torre J. Prediction of hydrodynamic and other solution properties of rigid proteins from atomic- and residue-level models. Biophys J 2011; 101:892-898. and Rocco M, Byron O. Hydrodynamic Modeling and Its Application in AUC. 1st ed. Elsevier Inc. Epub ahead of print 2015. DOI: 10.1016/bs.mie.2015.04.010.).

The sedimentation coefficient of AAV5-EP calculated from the coordinates by using the HydroPRO (Ortega A, Amoros D, Garcia De La Torre J. Prediction of hydrodynamic and other solution properties of rigid proteins from atomic- and residue-level models. Biophys J 2011; 101:892-898.) program was 65.7 S (s20,w=67.7 S), which is reasonably consistent with the experimentally obtained value (67.3 S).

The $f/f_0$ values of AAV5-EP and AAV5-FP were clearly different from each other, wherein that of AAV5-EP was 1.35 and that of AAV5-FP was 1.24. These experimental s values were values close to $f/f_0$=1.3, which is the value for a T=1 viral capsid reported in previous studies (Caston J R, Ghabrial S A, Jiang D, et al. Three-dimensional structure of *Penicillium chrysogenum* virus: A double-stranded RNA virus with a genuine T=1 capsid. J Mol Biol 2003; 331:417-431. and Gomez-Blanco J, Luque D, Gonzalez J M, et al. *Cryphonectria nitschkei* Virus 1 Structure Shows that the Capsid Protein of Chrysoviruses Is a Duplicated Helix-Rich Fold Conserved in Fungal Double-Stranded RNA Viruses. J Virol 2012; 86:8314-8318). It needs to be noted that $f/f_0$ is not equal to 1.0 because the $f_0$ value is the friction coefficient of a particle having a spherical shape and in an unhydrated state.

Determination of Wavelength Dependence of UV Absorption of AAV5-EP Particle and AAV5-FP Particle from SV-AUC The wavelength dependence of the total peak areas in the c(s) distributions at each measurement wavelength of AAV5-EP and AAV5-FP completely overlapped with the ultraviolet spectra of AAV5-EP and AAV5-FP, respectively, measured by using an ultraviolet spectrophotometer. Accordingly, it was shown that the absorption spectrum of each component was successfully acquired by SV-AUC c(s) analysis.

(1) Multi-Wavelength Absorbance Data and Refractive Index Data of AAV5 Samples

AAV5-FP (full particle) and AAV5-EP (empty particle) were produced from host cells transfected with an AAV5-FP vector and an AAV5-EP vector, respectively, and purified. Purified AAV5-EP was concentrated using Amicon Ultra 0.5 equipped with a 30 kDa filter membrane (Merck Millipore, US) to an absorbance of 0.95 at 280 nm at an optical path length of 1 cm. Similarly, recovered AAV5-FP was concentrated to an absorbance of 0.75 at 260 nm. AAV5-FP and AAV5-EP were mixed such that the ratio of the numbers of particles of AAV5-FP to AAV5-EP (=[number of particles of AAV5-EP]/[number of particles of AAV5-FP]) was 1.2, to prepare an AAV5 sample in PBS.

Measurement cells were filled with the prepared AAV5 sample and subjected to density contrast sedimentation velocity analytical ultracentrifugation (SV-AUC). The time-dependent sedimentation behavior in the measuring cells during centrifugation was acquired by measurement with ultraviolet (UV) and interference (IF) detection systems scanning at 11 measurement wavelengths (230 nm, 235 nm, 240 nm, 245 nm, 250 nm, 255 nm, 260 nm, 270 nm, 275 nm, 280 nm) (2.1 in FIG. 12). FIG. 2 shows measurement results of the time-dependent sedimentation behavior obtained from the wavelengths reflecting the properties of a protein or a nucleic acid, that is, the measurement wavelengths of the peptide bond absorption region (around 230 nm), the nucleic acid absorption region (around 260 nm), and the aromatic amino acid absorption region (around 280 nm), among the 11 measurement wavelengths.

Figure 3C:
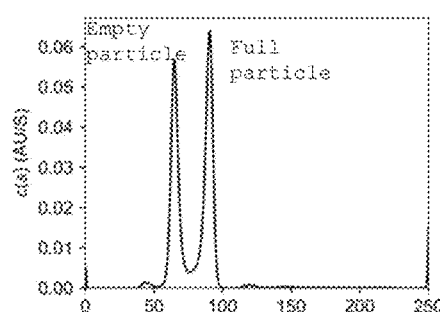
FIG. 3C is a diagram showing sedimentation coefficient distributions of AAV5 samples based on absorbance measurement at 280 nm.
Figure 3C:
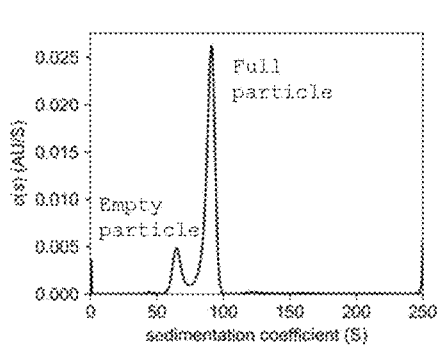
Figure 3C:
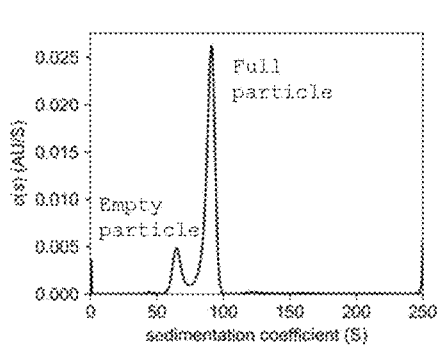
Figure 4:
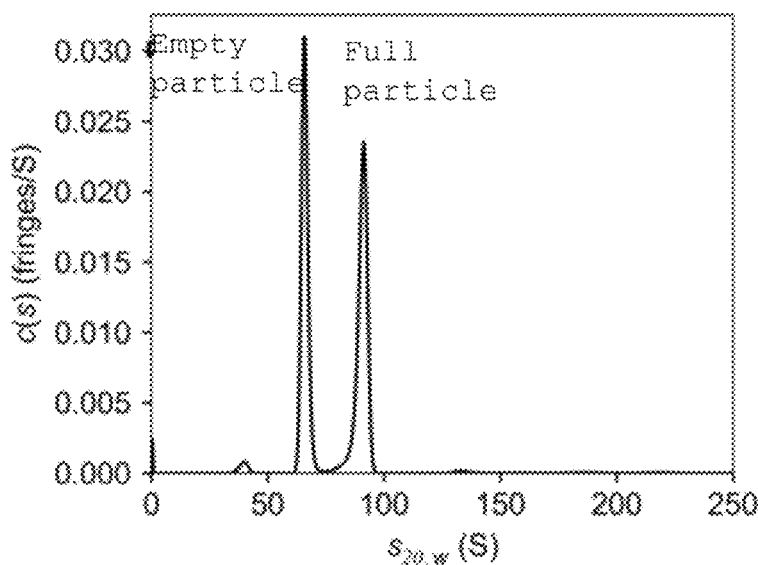
FIG. 4 is a diagram showing sedimentation coefficient distributions of AAV5 samples based on refractive index measurement.

(2) Sedimentation Coefficient Distributions of AAV5 Samples by Sedimentation Behavior Analysis Distributions of the sedimentation coefficient C(s) from the absorbance data obtained by the measurement with the UV detection system according to the analysis method described in the section "Data analysis of SV-AUC" were each obtained (2.2 in FIG. 12). FIGS. 3A to 3C show sedimentation coefficient distributions at measurement wavelengths of 230 nm, 260 nm, and 280 nm, respectively. Similarly, a sedimentation coefficient distribution was obtained from the refractive index data obtained by the measurement with the interference detection system (FIG. 4).

FIG. 3A mainly shows a peak at a sedimentation coefficient of 67.3 S and a peak at a sedimentation coefficient of 97.3 S. When a sedimentation coefficient distribution was obtained for a sample of AAV5-EP (empty particle) alone in the same manner as in the present Example, a peak at 67.3 s was mainly observed. In addition, when a sedimentation coefficient distribution was obtained for a sample of AAV5-FP (full particle) alone, a peak at 97.3 S was mainly observed. These results show that the two main peaks observed in FIG. 3A correspond to AAV5-EP and AAV5-FP. The present Example shows that AAV5-EP and AAV5-FP can each be separated and identified by sedimentation of an AAV5 sample, a mixture of AAV5-EP and AAV5-FP, in a centrifugal force field.

FIGS. 3A to 3C show that the sedimentation coefficients of the peaks of AAV5-FP and AAV5-EP have the same values even at different measurement wavelengths such as 230 nm, 260 nm, and 280 nm. FIGS. 3A to 3C and FIG. 4 show that the sedimentation coefficients of the peaks of AAV5-FP and AAV5-EP have corresponding values even with different detection systems, such as a UV detection system and an IF detection system.

(3) Concentration of Virus Particle of Each of AAV5-FP and AAV5-EP Based on Refractive Index Data The increments in refractive index ($\delta d$) of AAV5-FP and AAV5-EP were divided by the specific refractive index increments per concentration (dn/dc), respectively, to obtain the gram concentrations of AAV5-FP and AAV5-EP, respectively, and further, the gram concentrations were divided by the molecular weights thereof, respectively, to determine the molar concentrations of the virus particles, respectively (2.4 in FIG. 12).

(4) Absorbance Spectrum of Each of AAV5-FP and AAV5-EP based on Absorbance Data

Figures 5A, 5B:
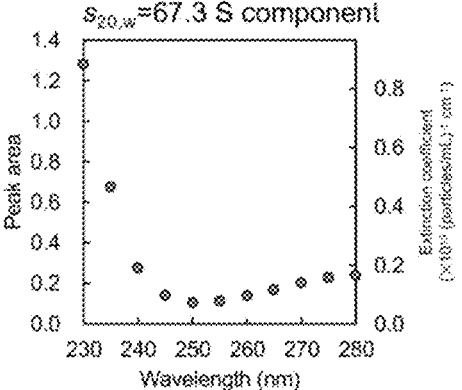
FIG. 5A is a scatter diagram showing a molar absorption spectrum of an empty particle.
FIG. 5B is a scatter diagram showing a molar absorption spectrum of a full particle.

The area of the peak corresponding to AAV5-FP in the sedimentation coefficient distribution at a specific measurement wavelength was calculated to obtain the absorbance of AAV5-FP at that measurement wavelength (2.3 in FIG. 12). Similarly, the absorbance of AAV5-FP at each measurement wavelength was obtained. The obtained absorbance (peak area) was plotted against the measurement wavelength to obtain an absorbance spectrum (left vertical axis in FIG. 5A). Similarly, the absorbance spectrum of AAV5-EP was obtained (left vertical axis in FIG. 5B).

The absorbances of AAV5-FP at measurement wavelengths obtained above were divided by the virus particle concentrations of the AAV5-FP particle at the measurement wavelengths obtained in step (3) above, respectively, to calculate the extinction coefficients of AAV5-FP at the measurement wavelengths, respectively. The calculated extinction coefficients were plotted against the measurement wavelengths to obtain an extinction coefficient spectrum (right vertical axis in FIG. 5A). Similarly, the extinction coefficient spectrum of AAV5-EP was obtained (right vertical axis in FIG. 5B).

Comparison of Purity Evaluation Between SV-AUC and A260/A280 Ratio of AAV Samples A260/A280 is commonly used to evaluate virus purity. Similarly, for an AAV sample, Sommer et al. have proposed a method for estimating the proportion of a full particle in all particles by using this parameter (Sommer J M, Smith P H, Parthasarathy S, et al. Quantification of adeno-associated virus particles and empty capsids by optical density measurement. Mol Ther 2003; 7:122-128). This is a simple method for determining purity based on a UV measurement, but as indicated by other previous studies (Dobnik D, Kogovsek P, Jakomin T, et al. Accurate quantification and characterization of adeno-associated viral vectors. Front Microbiol; 10. Epub ahead of print 2019. DOI: 10.3389/fmicb.2019.01570, Lock M, Alvira M R, Wilson J M. Analysis of particle content of recombinant adeno-associated virus serotype 8 vectors by ion-exchange chromatography. Hum Gene Ther Methods 2012; 23:56-64, and Lock M, Alvira M R, Chen S, et al. Absolute Determination of Single-Stranded. 2014; 125:115-125), this method requires a high-purity sample, and it is challenging to estimate purity from A260/A280 when a molecule other than a full particle and an empty particle (for example, a DNA impurity or a protein contaminant) is included.

Figure 6:
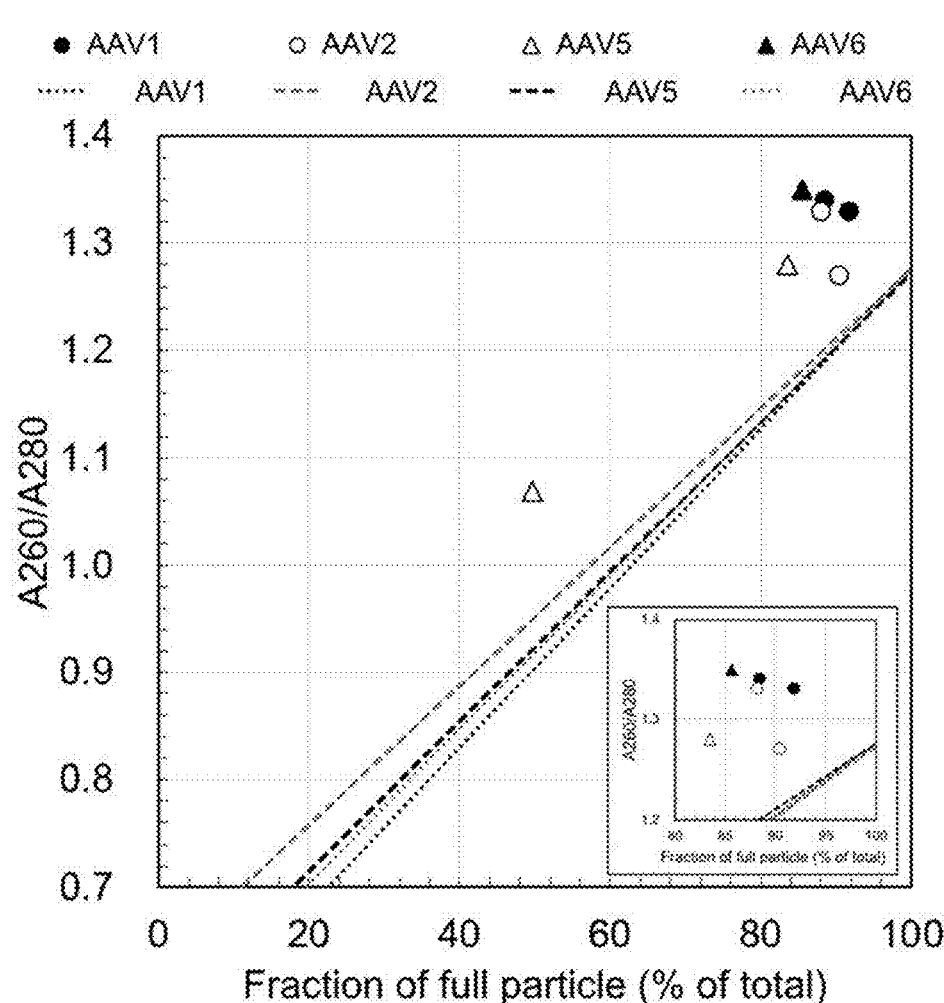
FIG. 6 is a diagram showing the correlation between A260/A280 measured with an ultraviolet absorptiometer and purity resulting from using an interference detection system using SV-AUC. The purity of each sample was calculated based on the result obtained by interference detection. A260/A280 was obtained from UV spectral measurement before the SV-AUC experiments. Black circles, white circles, white triangles, and black triangles represent AAV1-FP, AAV2-FP, AAV5-FP, and AAV6-FP, respectively. In addition, the line passing through A260/A280 of a full particle and an empty particle of each of serotypes AAV1-FP, AAV2-FP, AAV5-FP, and AAV6-FP is indicated by a black dotted line, a gray broken line, a black broken line, and a gray dotted line, respectively. No clear correlation was found in the samples tested in the present study.

In SV-AUC of the present Example, the ratios of A260 to A280 (A260/A280) of an AAV5-EP particle and an AAV5-FP particle were 0.58 and 1.27, respectively. These values were values close to the A260/A280 ratio (A260/A280=1.28) of AAV5-FP of the whole sample observed by using an ultraviolet spectrophotometer before the AUC experiment, but were values slightly smaller. In addition, samples including about 90% of a full particle were also analyzed for other serotypes (AAV1, AAV2, and AAV6). As a result, the correlation between the purity obtained by A260/A280 measured with an ultraviolet absorptiometer and the purity obtained by SV-AUC using an interference detection system was low (FIG. 6). These results show that it is difficult to estimate the purity of a sample including an unknown component other than an empty particle and a full particle by UV absorption measurement. On the other hand, SV-AUC enables a high degree of solute separation by sedimentation in a centrifugal force field. Thus, it can be deemed that SV-AUC provides a highly accurate determination of the purity of an AAV sample.

(5) Molar Extinction Coefficient Spectrum of Each of Empty Particle and Genomic DNA The molar extinction coefficient of each of AAV5-FP and AAV5-EP at each measurement wavelength was calculated according to the method described in the section "Determination of molar extinction coefficient" (2.5 in FIG. 12). The calculated molar extinction coefficient of AAV5-EP was plotted against each measurement wavelength to obtain a molar extinction coefficient spectrum of AAV5-EP (○ in FIG. 7).

AAV5-FP includes a capsid of the virus particle (AAV5-EP) and the genome single-stranded DNA (ssDNA). The molar extinction coefficient of the genomic DNA of AAV5 at each measurement wavelength was estimated by subtracting the molar extinction coefficient of AAV5-EP from the molar extinction coefficient of AAV5-FP. The estimated molar extinction coefficient of ssDNA was plotted against each measurement wavelength to obtain a molar extinction coefficient spectrum of ssDNA (Δ in FIG. 7).

(6) Isosbestic Point Between Capsid and ssDNA of AAV5

Figure 7:
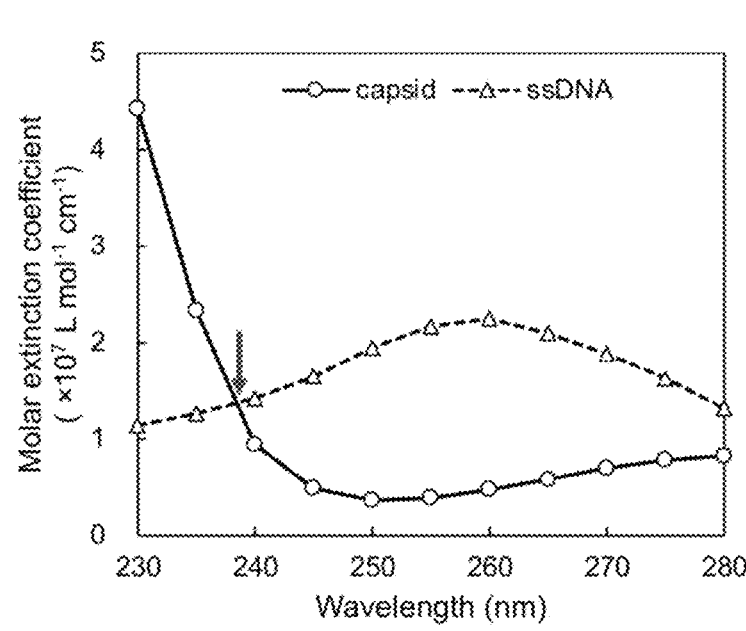
FIG. 7 is a diagram showing a molar extinction coefficient spectrum of AAV-EP and a molar extinction coefficient spectrum of ssDNA. The intersection of the AAV-EP molar extinction coefficient spectrum and the ssDNA molar extinction coefficient spectrum represents an isosbestic point (239 nm) (arrow).

The isosbestic point between the capsid of the virus particle (AAV5-EP) and the genome ssDNA can be obtained from the intersection of the molar extinction coefficient spectrum of AAV5-EP and the molar extinction coefficient spectrum of ssDNA, and the value thereof was 239 nm (FIG. 7 and 2.6 in FIG. 12).

At the isosbestic point, the molar extinction coefficient of the capsid of the virus particle is equal to molar extinction coefficient of the genome ssDNA ($\varepsilon_{capsid}=\varepsilon_{ssDNA}$), and thus by calculating their respective absorbances ($Area_{AAVfull}$ and $Area_{AAVempty}$) in a mixture of AAV5-FP, which consists of a capsid of the virus particle and genomic DNA, and the capsid of the virus particle (AAV5-EP) and using the following equation, it is possible to determine the ratio between an AAV5-FP virus particle and an AAV5-EP virus particle (ratio of the numbers of particles) without calculating the molar extinction coefficients of AAV5-FP and AAV5-EP.

$$\frac{[N_{AAVempty}]}{[N_{AAVfull}]} = \frac{2 \times Area_{capsid}}{Area_{capsid} + Area_{ssDNA}} = \frac{2 \times Area_{AAVempty}}{Area_{AAVfull}} \quad \text{Equation 15}$$

where $N_{AAVempty}$ and $N_{AAVfull}$ represent the numbers of particles of AAV-EP and AAV-FP, respectively, and $Area_{AAVempty}$ ($=Area_{capsid}$) and $Area_{AAVfull}$ ($=Area_{capsid}+Area_{ssDNA}$) represent the area of the peak corresponding to AAV5-EP and the area of the peak corresponding to AAV-FP, respectively, in the sedimentation coefficient distribution.

(7) Quantitative Ratio Between AAV5-FP and AAV5-EP in AAV5 Sample

Figure 8:
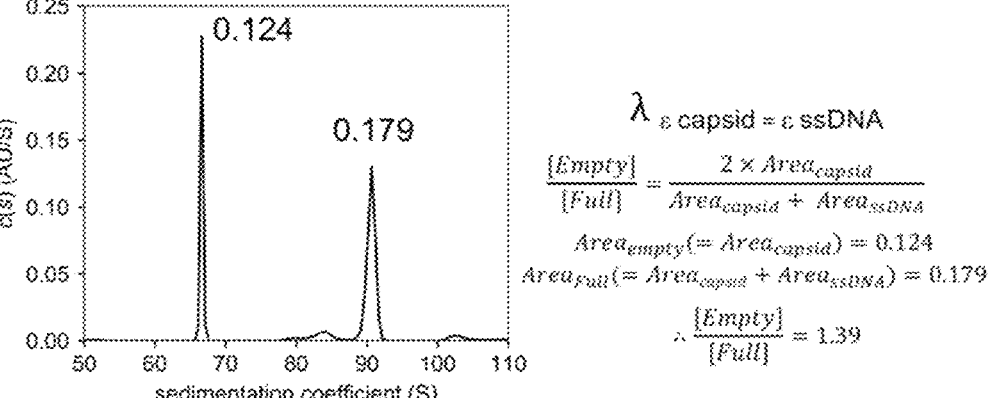
FIG. 8 is a diagram showing the absolute number ratio of the numbers of virus particles between AAV5-FP and AAV5-EP in AAV5 samples, measured only at an isosbestic point of 239 nm.

The ratio of the numbers of virus particles between AAV5-EP and AAV5-FP is determined by using the isosbestic point (=wavelength of 239 nm) obtained in step (6) above, without using the molar extinction coefficient (3.1 and 3.2 in FIG. 12). Specifically, by measuring an AAV5 sample at the isosbestic point to acquire absorbance data (partially corresponding to step (1)), obtaining a distribution of sedimentation coefficient C(s) from the absorbance data to identify the peak corresponding to AAV5-FP and the peak corresponding to AAV5-EP (partially corresponding to step (2)), and obtaining the absorbance of AAV5-FP and the absorbance of AAV5-EP from the area of each peak (partially corresponding to step (4)), the absolute quantitative ratio of the numbers of virus particles between AAV5-FP and AAV5-EP in the AAV5 sample can be obtained (FIG. 8). FIG. 8 shows that the ratio between AAV5-FP and AAV5-EP in the AAV5 sample mixed such that the ratio of the numbers of particles of AAV5-EP to AAV5-FP was 1.2 was actually 1.2. As described above, the present Example shows that the ratio of the numbers of virus particles between AAV5-EP and AAV5-FP can be determined by using an isosbestic point, without acquiring absorbance data at a wavelength other than the isosbestic point, acquiring interference data, or calculating the molar extinction coefficient.

When a sedimentation coefficient distribution is prepared based on the absorbance data obtained by SV-AUC, a peak may be observed in the range of 70 S to 90 S between the peak at a sedimentation coefficient of 67.3 S corresponding to an empty particle and the peak at a sedimentation coefficient of 97.3 S corresponding to a full particle. It is considered that the peak observed in this range corresponds to an intermediate particle including a genomic DNA fragment inside the capsid of AAV5. Additionally, a peak may be observed in the range of 110 S to 120 S that is larger than the peak for a full particle. It is considered that the peak observed in this range corresponds to an aggregate including AAV5-FP. In the following, the identification of an intermediate particle and an aggregate was attempted using the extinction coefficient spectra of AAV5-EP and ssDNA obtained in step (5) above.

(8) Absorbance Spectrum of Component (Intermediate Particle and/or Aggregate) Other than AAV5-FP and AAV5-EP The area of the peak of the sedimentation coefficient corresponding to an intermediate particle in the sedimentation coefficient distribution at each measurement wavelength was calculated in the same manner as in step (4) above to obtain the absorbance of the intermediate particle at each measurement wavelength (4.2 in FIG. 12). The obtained absorbance was plotted against the measurement wavelength to obtain an absorbance spectrum of the intermediate particle. Similarly, the absorbance of an aggregate at each measurement wavelength was obtained and plotted against the measurement wavelength to obtain an absorbance spectrum of the aggregate.

(9) Number of ssDNA Bases Encapsulated in Intermediate Particle and/or Aggregate Multiple regression analysis based on Equation 9 was carried out on the absorbance spectrum of the intermediate particle obtained in step (8) above by using the molar extinction coefficient spectrum of ssDNA and the molar extinction coefficient spectrum of AAV5-EP (capsid of virus particle) obtained in step (5) above (4.3 in FIG. 12). As a result of the multiple regression analysis, $\alpha$ and $\beta$ in Equation 9 were determined. Using the determined $\alpha$ and $\beta$ in Equation 10 and Equation 11, respectively, the peak area of the capsid of the virus particle and the peak area of ssDNA were obtained. The obtained peak area of the capsid of the virus particle (=AAV-EP) was divided by the molar extinction coefficient thereof and the value (1.2) of the optical path length to calculate the concentration of the capsid of the virus particle in the peak corresponding to the intermediate particle. Similarly, the concentration of ssDNA in the peak corresponding to the intermediate particle was calculated from the obtained peak area of ssDNA. As described above, the number of ssDNA bases in the peak corresponding to the intermediate particle can be obtained (4.4 in FIG. 12). Once the number of bases of ssDNA is obtained, the weight (mg) of ssDNA can be calculated by multiplying the number thereof by the average molecular weight (300 M.W.) of the bases. In addition, by dividing the calculated ssDNA concentration by the calculated concentration of the capsid of the virus particle, the ratio of the number of bases of ssDNA to the number of capsid bases of the virus particle in the peak corresponding to the intermediate particle (=[number of ssDNA bases]/[number of capsid bases]) can also be obtained (4.4 in FIG. 12). When each capsid of virus particles included in the peak corresponding to the intermediate particle includes one ssDNA, the ratio of the number of ssDNA bases to the number of capsid bases of the virus particles corresponds to the ratio of the average nucleotide length of the ssDNA fragments included in the intermediate particle in the peak corresponding to the intermediate particle to the nucleotide length of the complete genomic ssDNA (=[nucleotide length of ssDNA fragments]/[nucleotide length of complete genomic ssDNA]).

In the same manner as in step (9) described for the intermediate particle, the number of ssDNA bases in the peak corresponding to the aggregate and the ratio of the number of ssDNA bases to the number of capsid bases of the virus particle in the peak corresponding to the aggregate can be obtained from the absorbance spectrum of the aggregate obtained in step (8) above (4.4 in FIG. 12).

The molecular weight, the partial specific volume, the s value, and the number of nucleotides for each combination of the number of capsids (=AAV-EP) ($n_{capside}$) and the number of ssDNA ($n_{ssDNA}$) were calculated (1.3 in FIG. 12). The molecular weight, the partial specific volume, the s value, and the number of nucleotides were calculated by using the molecular weight, the partial specific volume, and $f/f_0$ (=1.32) determined by AUC experiments using AAV5-EP and AAV5-FP (FIG. 9A). In addition, the sedimentation coefficient was estimated from the number of capsids or nucleic acid molecules (FIG. 9A). To estimate the sedimentation coefficient, the capsid composed of 60 viral proteins was normalized to 1, and the chain length of nucleic acid included in the full particle (=AAV-FP) was normalized to 1. The sedimentation coefficient can be calculated from the molecular weight, the partial specific volume, and the friction coefficient of a molecule, and thus by assuming values for these parameters, the sedimentation coefficient can be estimated. The number of ssDNA ($n_{ssDNA}$) was set to 0.5, 1.0, 1.5, 2.0, 2.5, or 3.0, and the number of capsids ($n_{capsid}$) was set to 1.0, 2.0, or 3.0 to estimate the sedimentation coefficient for each combination of these numbers (FIG. 9A). By comparing this estimate with the ratio of the capsid to the nucleic acid as an experimental value (4.3 in FIG. 12), for a peak that can correspond to an unknown particle type (for example, aggregate) observed in the sedimentation coefficient distribution, the proportion of the capsid and/or ssDNA in the particle type can be calculated.

The estimated sedimentation coefficients for the number of nucleotides (or the number of bases of ssDNA) were plotted on a graph with the sedimentation coefficient on the horizontal axis and the number of nucleotides on the vertical axis to obtain a scatter diagram (FIG. 9B). FIG. 9B suggests that the particle type observed at a sedimentation coefficient of 65 to 95 S is capsid monomer+ssDNA (full particle), suggests that the particle type observed at 95 to 120 S is capsid monomer+ssDNA (full particle) or capsid dimer+ssDNA, suggests that the particle type observed at 120 to 140 S is capsid dimer+ssDNA or capsid trimer+ssDNA, and suggests that the particle type observed at 140 to 160 S is capsid trimer+ssDNA.

As can be understood from FIG. 9B, in a sedimentation coefficient range (for example, 95 S or more) in which a plurality of particle association states can exist, it is usually impossible to determine the absolute ratio of the number of capsids to the number of ssDNA from the value of the sedimentation coefficient. In addition, even in multi-wavelength analytical ultracentrifugation, the molar ratio of capsids to ssDNA can be determined, but the absolute ratio of the number of capsids to the number of nucleic acids (stoichiometry of capsids and nucleic acids) cannot be determined, only by spectral resolution plotting the peak areas of the sedimentation coefficients acquired. Therefore, the scatter diagram (FIG. 9B) showing the relationship between the number of bases of ssDNA and the sedimentation coefficient described above is combined with the number of nucleic acid bases obtained from spectral resolution of the peak area plot for an impurity (for example, a capsid aggregate, a free nucleic acid, or a protein) acquired by multi-wavelength analytical ultracentrifugation (FIG. 9C and 4.3 in FIG. 12) to identify the impurity. This makes it possible to determine the ratio of the number of capsids to the number of ssDNA even in a sedimentation coefficient range in which a plurality of particle association states can exist. In fact, it was determined that the particle type observed around 115 S (FIG. 9C) was not a particle type in which one or more molecules of ssDNA were included in a capsid monomer, but a dimer consisting of an intermediate particle-intermediate particle or a dimer consisting of an intermediate particle-full particle.

Further, the numbers of nucleotides included in the peaks corresponding to an empty particle (AAV5-EP), an intermediate particle, a full particle (AAV5-FP), and an aggregate were each calculated by using Equation 14 (4.5 in FIG. 12). The calculated number of nucleotides was plotted against the sedimentation coefficient of each peak (FIG. 9C). It is known that there is a good correlation between the sedimentation coefficient of AAV and the number of encapsulated nucleotides (Burnham B, Nass S, Kong E, et al. Analytical Ultracentrifugation as an Approach to Characterize Recombinant Adeno-Associated Viral Vectors. Hum Gene Ther Methods 2015; 26:228-242, and Nass S A, Mattingly M A, Woodcock D A, et al. Universal Method for the Purification of Recombinant AAV Vectors of Differing Serotypes. Mol Ther—Methods Clin Dev 2018; 9:33-46). As shown in FIG. 9C, the relationship between the sedimentation coefficients and the numbers of encapsulated nucleotides in an empty particle, an intermediate particle, and a full particle of AAV5 (Δ and ▲ in FIG. 9C) calculated in the present Example matched the previously reported correlation (broken line in FIG. 9C). This result shows that the SV-AUC analysis method used in the present Example is appropriate.

For AAV1, AAV2, and AAV6, which are serotypes other than AAV5, the relationship between the sedimentation coefficients of AAV and the number of encapsulated nucleotides was investigated. As shown in FIG. 9C, for not only AAV5 but also AAV1 (○ and ●), AAV2 (□ and ■), and AAV6 (◇), the relationship between the sedimentation coefficients and the numbers of encapsulated nucleotides in an empty particle, an intermediate particle, and a full particle calculated by the analysis method of the present Example matched the previously reported correlation. These results show that the SV-AUC analysis method used in the present Example is appropriate regardless of the AAV serotype.

For virus particle groups in the sedimentation coefficient range of 110 S to 120 S, no clear correlation was found between the sedimentation coefficients and the number of nucleotides (FIG. 9C). This result suggests that the virus particle groups that exhibited a sedimentation coefficient in the range of 110 S to 120 S are not AAV monomers including two or more molecules of ssDNA (for example, ssDNA dimers). It is estimated that these particle groups are each a homogeneous dimer assembly (such as empty particle-empty particle, full particle-full particle, or intermediate particle-intermediate particle) or a heterogeneous dimer assembly (such as empty particle-intermediate particle, empty particle-full particle, or intermediate particle-full particle), considering that the sedimentation coefficient of an AAV sample calculated by using the equation describing the relationship between the sedimentation coefficient and the oligomeric state given by Garcia et al. (De La Torre J G, Bloomfield VA. Hydrodynamic properties of complex, rigid, biological macromolecules: Theory and applications. Q Rev Biophys 1981; 14:81-139) is 97 S for an EP-EP dimer, 136 S for an FP-FP dimer, 165 S for an FP linear trimer, or 175 S for an FP triangular trimer.

The present Example has shown that the combined analytical approach of multiple regression analysis and SV-AUC used in the present Example is a useful method that can enable direct determination of the ratio of the capsid to the nucleic acid and enable estimation of what virus particle a virus particle group in the range of 110 S to 120 S is. According to the method used in the present Example, not only an empty particle, an intermediate particle, a full particle, and an aggregate, but also genomic ssDNA or an aggregate of an empty particle can be characterized as long as those components can be separated and detected by SV-AUC.

Figures 10A, 10B:
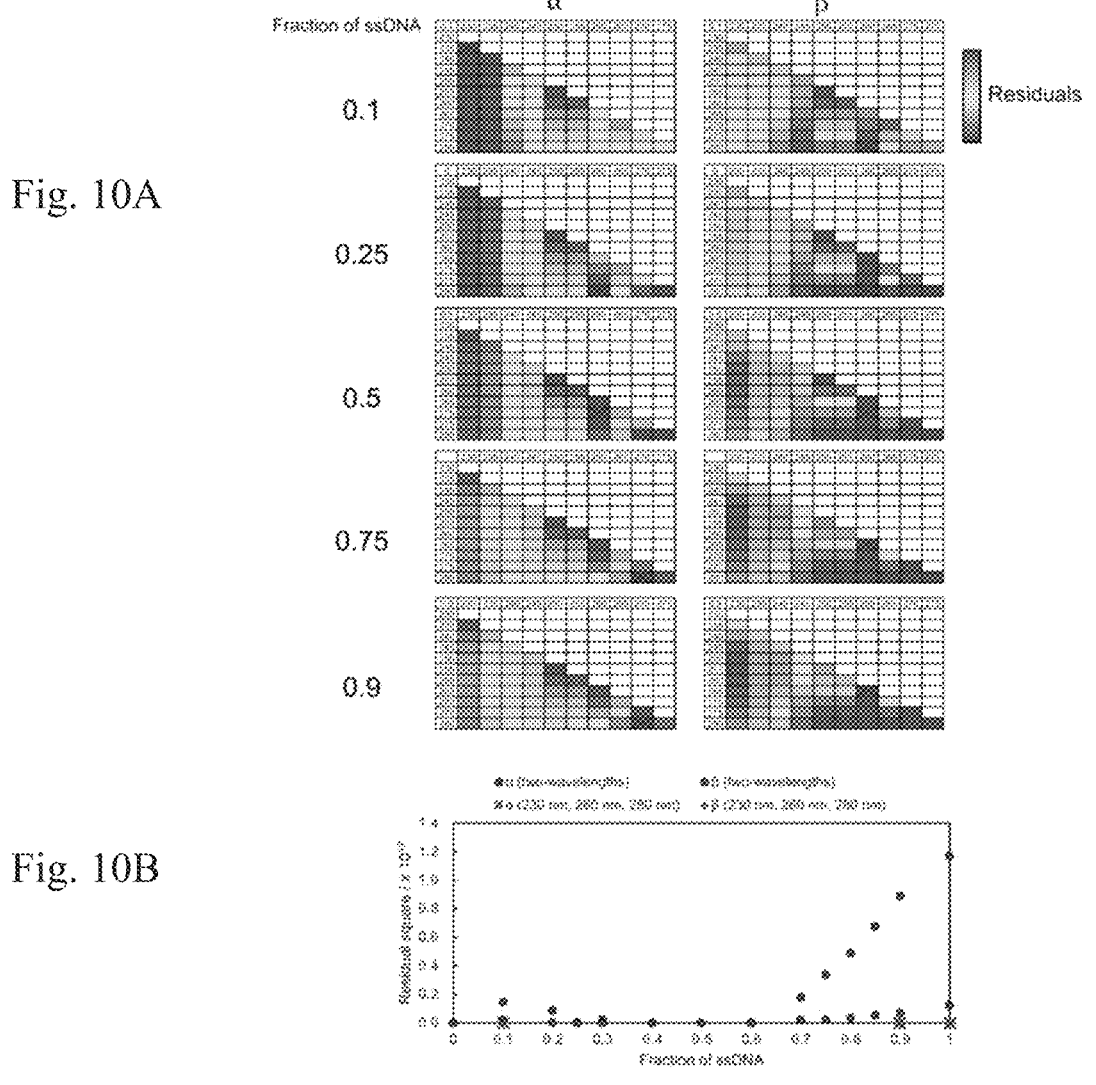
FIG. 10A is a heat map comparing the residuals α (left) and β (right) of the partial regression coefficients of Equation 9 to Equation 11 below with the residuals obtained from the detection of each fraction of ssDNA at 11 wavelengths.
FIG. 10B is a diagram showing residual squared plots of partial regression coefficients at each fraction of ssDNA.

The appropriate measurement wavelength for the multiple regression analysis in step (9) above was assessed. By using data obtained by two-wavelength detection of several ssDNA fractions, the partial regression coefficients (α for capsid and β for ssDNA) shown in Equation 9 were calculated. The calculated coefficients were compared with those calculated using data derived from an 11-wavelength detection method. As a result, in the ssDNA fraction range of 0.25 to 0.6, the above-calculated coefficients were reasonably consistent with the coefficients calculated by using the data obtained from the 11-wavelength detection method (○ and ● in FIG. 10B). When the ssDNA fraction was 0.7 or more, a residual increase in a was observed (○ in FIG. 10B). This result shows that using three or more wavelength detections is preferable to determine the ssDNA content of an unknown intermediate particle.

By carrying out such an examination, the validity of the measurement wavelength selection can be evaluated. For example, it can be seen that the partial regression coefficients can be determined with relatively high accuracy by selecting wavelengths reflecting the properties of a protein or a nucleic acid, that is, three wavelengths each from the peptide bond absorption region (around 230 nm), the nucleic acid absorption region (around 260 nm), and the aromatic amino acid absorption region (around 280 nm) (× and + in FIG. 10B).

As described above, in the present embodiment, the data acquired by SV-AUC is processed by the program SEDFIT. Then, various analyses are carried out based on the processing results. It would be convenient to have a computer program for automatically or semi-automatically executing these analyses. For example, when a sedimentation coefficient distribution obtained by SEDFIT is input, a computer program that automatically executes, or semi-automatically executes while receiving an instruction from the user, at least a part of steps (3) to (9) above by using the sedimentation coefficient distribution is envisioned. This computer program may have the same functions as SEDFIT to carry out the above analyses without SEDFIT.

The above computer program has the function of preparing various graphs, as shown in FIG. 1 to FIG. 10, based on the processing results and displaying the graphs on a display device. This allows the user to easily visually confirm the processing results.

In addition, the above computer program has the function of storing the processing results in a storage device in a manner that makes these results distinguishable from other processing results. In this case, the computer program can, for example, extract a plurality of specific processing results from among the processing results stored in the storage device, and correlate the various graphs related to the extracted processing results therewith to display the graphs on the display device. This allows the user to compare the processing results of each sample and to check changes over time in the processing results of the same sample.

The above computer program is assumed to be installed and used in an information processing device such as a personal computer and a tablet terminal, which is a separate device from SV-AUC. However, the computer program may be installed in SV-AUC and used.

51

Figure 11:
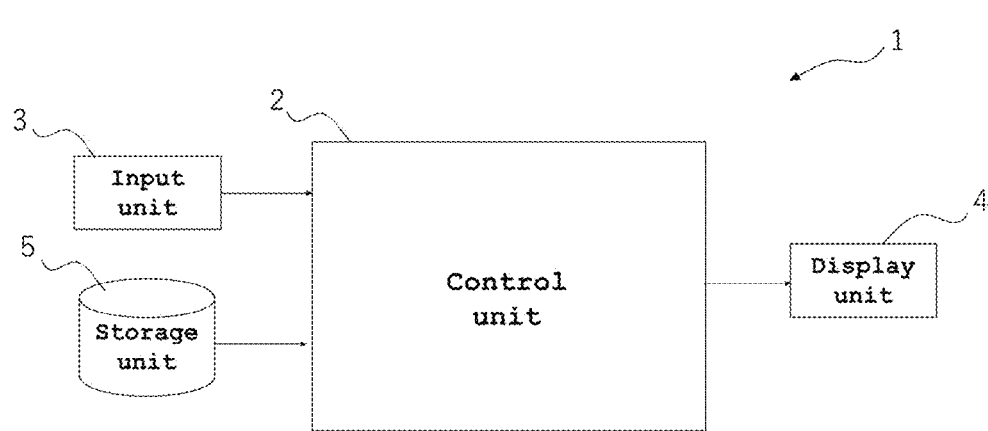
FIG. 11 is a block diagram of an apparatus that practices a method according to one embodiment of the present invention.

FIG. 11 is a block diagram of an apparatus (computer) 1 that executes the method of the above embodiment.

Apparatus 1 includes a control unit (processor) 2, an input unit 3, a display unit 4, and a storage unit 5. The control unit 2 performs arithmetic processing and control of the entire apparatus. The input unit 3 is a section that generates or receives input data for apparatus 1, and is composed of, for example, a keyboard, a mouse, or a touch panel. Display unit 4 is a section that displays processing results and the like by the control unit 2, and is composed of, for example, a liquid crystal display, an organic EL display, or a plasma display. Storage unit 5 stores a program that runs on the control unit (processor) 2, parameter data required for executing the method of the present embodiment, and the like. These control unit 2, input unit 3, and display unit 4 are interconnected by appropriate buses not shown. The apparatus 1 comprises an information processing device such as a desktop computer, a notebook computer, a workstation, or a tablet terminal.

The control unit 2 includes, for example, a CPU (Central Processing Unit) or MPU (Micro Processing Unit) that cooperates with software to realize a predetermined function. The control unit 2 reads data or a program stored in the storage unit 5 and loads the same into the control unit 2 to cause the apparatus 1 to execute the method of the above embodiment. The program loaded into the control unit 2 may be provided from a communication unit or the like that performs communication according to a predetermined communication standard, or may be stored in a portable recording medium (computer-readable medium).

The control unit 2 acquires the above various optical data as input data, executes each processing shown in the method of the above embodiment, calculates the above molar concentration, molar extinction coefficient, quantitative ratio, degree of contribution, proportion, concentration, absorbance ratio, molecular weight, and the like as output data, or presents a determination of the quality, and displays the same on the display unit 4. That is, the above computer program has the function of preparing various graphs, as shown in FIG. 1 to FIG. 10, based on the processing results and displaying the graphs on the display unit 4. This allows the user to easily visually confirm the processing results.

In addition, the above computer program has the function of storing the processing results in the storage unit 5 in a manner that makes these results distinguishable from other processing results. In this case, the computer program can, for example, extract a plurality of specific processing results from among the processing results stored in the storage unit 5, and correlate the various graphs related to the extracted processing results therewith to display the graphs on the display unit 4. This allows the user to compare the processing results of each sample and to check changes over time in the processing results of the same sample.

The above computer program may be installed and used in an information processing device such as a personal computer and a tablet terminal, a separate device from SV-AUC. In addition, the computer program may be installed in SV-AUC and used.

REFERENCE SIGNS LIST 1 apparatus (computer)
2 control unit (processor)
3 input unit
4 display unit
5 storage unit

52

The invention claimed is:

1. A method for characterizing a molecule delivery particle, wherein the first particle comprises a first coat and a first delivery molecule, and the second particle comprises a second coat; the method comprising:
subjecting a molecule delivery particle comprising a first particle and a second particle to particle separation with optical measurement to determine an increment in refractive index of each of the first particle and the second particle; and
determining a molar concentration of each of the first particle and the second particle based on the increment in refractive index, a molecular weight, and a specific refractive index increment of each of the first particle and the second particle;
wherein the method comprises:
subjecting the molecule delivery particle to particle separation with optical measurement at a plurality of measurement wavelengths to determine an absorbance of each of the first particle and the second particle for each measurement wavelength of the plurality of measurement wavelengths; and
determining a molar extinction coefficient of each of the first particle and the second particle for the each measurement wavelength based on the absorbance of each of the first particle and the second particle and the molar concentration of each of the first particle and the second particle;
and the method comprises:
determining a molar extinction coefficient of the first particle and the second particle for the each measurement wavelength based on the absorbance of each of the first particle and the second particle and the molar concentration of each of the first particle and the second particle; and
determining a molar extinction coefficient of the first delivery molecule for the each measurement wavelength by subtracting the molar extinction coefficient of the second particle from the molar extinction coefficient of the first particle.

2. The method according to claim 1, wherein the method comprises:
identifying an isosbestic point at which the molar extinction coefficient of the second particle and the molar extinction coefficient of the first delivery molecule are consistent with each other; and
determining a quantitative ratio between the first particle and the second particle by using the absorbance of each of the first particle and the second particle at the isosbestic point.

3. The method according to claim 2, wherein the method comprises determining that the molecule delivery particle has a predetermined quality when the quantitative ratio exceeds a first threshold.

4. The method according to claim 1, wherein the molecule delivery particle further comprises a third particle, and the third particle comprises a third coat and optionally comprises a third delivery molecule; and
the method comprises:
determining an absorbance of the third particle for the each measurement wavelength by particle separation with optical measurement of the molecule delivery particle; and
determining a degree of contribution of the molar extinction coefficient of the second particle and the molar extinction coefficient of the first delivery molecule to the absorbance of the third particle.

5. The method according to claim 4, wherein the method further comprises: determining a proportion of the third particle; and/or determining a concentration of each of the third coat and the third delivery molecule, based on the degree of contribution.

6. The method according to claim 5, wherein the method comprises determining a quantitative ratio of the first particle or the second particle to the molecule delivery particle based on the molar concentration of the first particle, the molar concentration of the second particle, the concentration of the third coat, and the concentration of the third delivery molecule, and determining that the molecule delivery particle has a predetermined quality when the quantitative ratio exceeds a first threshold.

7. The method according to claim 1, wherein the particle separation is centrifugation, chromatography, or field flow fractionation.

8. The method according to claim 1, wherein the molecule delivery particle is a virus particle, a liposome, an albumin particle, a micelle, or a polylactic acid-glycolic acid copolymer particle.

9. The method according to claim 8, wherein the virus particle is an adeno-associated virus, an adenovirus, a herpes virus, a Sendai virus, a stealth virus, a lentivirus, or a retrovirus.

10. A program that, when loaded into a control unit of a computer, causes the computer to execute the method according to claim 1.

\*  \*  \*  \*  \*